(12) United States Patent
Wei

(10) Patent No.: US 10,722,477 B2
(45) Date of Patent: *Jul. 28, 2020

(54) COOLING ADJUNCT FOR MEDICATIONS TO TREAT DISORDERS IN THE NASAL CAVITY

(71) Applicant: Edward Tak Wei, Berkeley, CA (US)

(72) Inventor: Edward Tak Wei, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/530,976

(22) Filed: Mar. 31, 2017

(65) Prior Publication Data
US 2017/0296489 A1 Oct. 19, 2017

Related U.S. Application Data

(63) Continuation-in-part of application No. 14/545,014, filed on Mar. 16, 2015, now Pat. No. 9,642,868, which is a continuation-in-part of application No. 14/544,355, filed on Dec. 29, 2014, now Pat. No. 10,195,217.

(51) Int. Cl.
| | |
|---|---|
| *A61K 9/00* | (2006.01) |
| *A61K 31/66* | (2006.01) |
| *A61K 31/56* | (2006.01) |
| *A61K 47/02* | (2006.01) |
| *A61M 11/00* | (2006.01) |
| *A61M 15/00* | (2006.01) |
| *A61F 13/40* | (2006.01) |
| *A61K 31/075* | (2006.01) |

(52) U.S. Cl.
CPC .......... *A61K 31/075* (2013.01); *A61K 9/0043* (2013.01); *A61K 31/56* (2013.01); *A61K 31/66* (2013.01); *A61M 11/007* (2014.02); *A61K 47/02* (2013.01); *A61M 15/00* (2013.01); *A61M 35/006* (2013.01); *A61M 2210/0618* (2013.01)

(58) Field of Classification Search
CPC ...... A61K 31/075; A61K 31/56; A61K 31/66; A61K 31/00; A61K 9/0043; A61K 31/662; A61M 11/007; A61M 2210/0618; A61M 35/006
See application file for complete search history.

(56) References Cited

U.S. PATENT DOCUMENTS

2012/0149690 A1* 6/2012 Dang .................. A61K 9/0043
514/217.05

OTHER PUBLICATIONS

Horak, "Effectiveness of twice daily azelastine nasal spray in patients with seasonal allergic rhinitis", Therapeutics and Clinical Risk Management 2008: 4(5), pp. 1009-1022.*

* cited by examiner

*Primary Examiner* — Rachael E Bredefeld

(57) ABSTRACT

The present discovery pertains generally to the field of therapeutic compounds. More specifically the present discovery pertains to certain di-alkyl-phosphinoyl-alkanes as described herein, DIPA-1-8 and DIPA-1-9, and 2-6 and 2-7 that are collectively referred to herein as "DAPA compounds", that are useful in the treatment of disorders (e.g., diseases) including: sensory discomfort (e.g., caused by inflammation, irritation, itch, or pain) in the nasal cavity. The applicant has found that localized delivery of DAPA compounds in combination with an intranasal steroid or an intranasal antihistamine immediately relieves nasal discomfort and enhances patient adherence to the use of the nasal medications.

8 Claims, 3 Drawing Sheets

COOLING ADJUNCT FOR MEDICATIONS TO TREAT DISORDERS IN THE NASAL CAVITY

CROSS-REFERENCE TO RELATED APPLICATIONS

This application is a continuation-in-part of U.S. Ser. No. 14/545,014 filed Mar. 16, 2015.

BACKGROUND OF THE INVENTION

Field of the Invention

The present invention pertains generally to the formulation of therapeutic compounds for treatment of disorders of the nasal cavity. More specifically the present invention pertains to use of certain cooling agents that are useful in the relief of sensory discomfort originating from the nasal cavity and the incorporation of such cooling agents with another active ingredient in pharmaceutical compositions, and the use of these combinations for topical delivery of such compounds and compositions to the membranes of the nasal cavity.

Description of Related Art

Chemical sensory/cooling agents are molecules that can mimic the sensations of heat abstraction without a change in tissue temperatures. The exact sensations produced by chemicals depend on the selection of the active ingredient and the site and method of delivery. The term "chemical cooling agent" can be ambiguous because, for example, chemicals such as ethyl chloride as a gas, ethanol as a liquid, liquid nitrogen, or carbon dioxide as a solid, applied to the skin can evoke heat abstraction sensations by reducing tissue temperatures. In this application, chemical cooling agents will refer only to agents that elicit sensations of heat abstraction without a lowering of tissue temperatures.

The lining of the nasal membranes, called respiratory epithelium, is only one cell layer thick. At the base of this single layer are sensory nerve endings that are connected to the trigeminal sensory nerve. These nerve endings are highly sensitive to temperature, irritants, humidity, and osmotic pressure. One manifestation of nasal discomfort and inflammation is nasal stuffiness and congestion, and a sense of loss of patency and obstructed airflow. This condition can have many causes, the most common being "rhinitis", a technical term meaning the condition of inflammation of the membranes lining the nose. Rhinitis, especially allergic rhinitis, is characterized by nasal congestion, rhinorrhea ("runny nose"), sneezing, itching of the nose and/or postnasal drainage. A common form of rhinitis is seasonal allergic rhinitis which is caused by seasonal aeroallergens such as pollens and molds [Bousquet et al. Allergic Rhinitis and its Impact on Asthma Eur. J. Allergy Clin. Immunol. 63, 8-160 (2008); Seidman, M. D. et al. Clinical Practice Guideline: Allergic Rhinitis. Otolaryngol. Head Neck Surg. 152, S1-S43 (2015)]. Perennial allergic rhinitis is caused by perennial environmental aeroallergens such as dust mites, molds, animal allergens, or occupational allergens. Rhinitis can also be caused by food allergies. Some individuals, without evidence of allergic sensitization, will have rhinitis in reaction to nonspecific irritant stimuli such as cold dry air, perfumes, paint fumes, and cigarette smoke. This condition is called vasomotor rhinitis. Severe rhinitis may result from injury to the nasal membranes such as occurs after smoke inhalation, sinusitis, or after nasal surgery.

Rhinitis is also caused by the common cold virus. Initially, viral rhinitis is characterized by clear, watery rhinorrhea that is accompanied by sneezing and nasal obstruction. Edema of the nasal mucosa produces occlusion of the sinus ostia, with resulting facial pain, or of the Eustachian tube, with resulting ear fullness. Responsible viruses include rhinoviruses, respiratory syncytial virus, parainfluenza, influenza and adenoviruses. Fever may accompany viral rhinitis, especially if there is bacterial superinfection by streptococcal organisms.

The sinuses drain into the nasal cavity. Rhinosinusitis is inflammation of the mucosa of the nasal sinuses together with the nasal membranes. This condition is a major cause of breathing discomfort because it is accompanied by prolonged mucopurulent nasal discharge, facial pain and pressure, olfactory disturbance, and post-nasal drainage with cough. In rhinosinusitis, the causes of discomfort may infectious organisms such as bacteria and fungi. Hence, topical antibiotics, including anti-fungal agents may be applied, which have irritant properties of their own. Saline is also used for the irrigation of the sinuses. The large volume of liquid forced through the nasal cavity may cause mechanical discomfort.

Neoplastic diseases of the nasal cavity can also occur, including nasal carcinoma and metastases from the nasopharyngeal cavity. In these situations, cancer chemotherapeutic agents or radiation will cause rhinitis and sensory discomfort.

Rhinitis is a common symptom. There are approximately 60 million individuals with rhinitis each in the USA and in Europe, and about 30 million in Japan. The prevalence of allergic rhinitis, a subset of rhinitis, is estimated to be up to 20+% of the general population. The common cold also causes rhinitis and in the USA each person has one or two bouts of per year. The economic burdens of rhinitis associated with allocation of health resources, from loss of work days, and from absence at schools are significant [Stewart, M. et al. Epidemiology and burden of nasal congestion. Int. J. Gen. Med. 3, 37-45 (2010)].

Pharmacological management of some forms of rhinitis, especially allergic rhinitis, is a well-developed science. Effective topical medications for allergic rhinitis are the intra-nasally administered glucocorticosteroids [intranasal steroids], intranasal antihistamines, and sympathomimetic decongestants. Ancillary medications are the mast cell stabilizer, called sodium cromolyn, and ipratropium which reduces rhinorrhea but does not affect sneezing or itch. Other treatments include hypertonic saline or isotonic saline for nasal cavity irrigation. Sprays, nose drops, solutions, and gels are used for topical treatments of the nasal membranes to deliver the active ingredients and are familiar items of patient use for example, manual pump-operated metered atomizers (e.g. Flonase® and Nasacort®). Examples of leading corticosteroids used for allergic rhinitis are beclomethasone dipropionate, triamcinolone acetonide, budesonide, fluticasone propionate, mometasone furoate, ciclesonide, and fluticasone furoate. Examples of topical antihistamines are olopatadine and azelastine hydrochloride. The intranasal steroids and antihistamines reduce nasal membrane inflammation and the symptoms and signs of allergic rhinitis. Intranasal steroids are not effective for relieving the discomforts of infectious [e.g. viral] rhinitis, and have limited efficacy for the rhinitis caused by rhinosinusitis. Intranasal steroids and antihistamines are less effective for rhinitis caused by air pollutants wherein irritants directly damage the nasal mucosa.

Menthol, camphor and eucalyptus oil have been used since ancient times as remedies for nasal irritation and for refreshment of nasal sensations. These compounds may briefly provide cooling sensations in the nasal passages but are not effective for rhinitis. In fact these substances exacerbate nasal congestion and obstruction, especially in the late and delayed stages of rhinitis. In the laboratory, menthol is an irritant when instilled into the nasal passages of humans [Alenmyr, L. et al. TRPV1 and TRPA1 stimulation induces MUC5B secretion in the human nasal airway in vivo. Clin. Physiol. Funct. Imaging 31, 435-444 (2011)]. Menthol vapor delivered onto the membranes of the nasopharynx via orthograde or retrograde airflow [in the form of a menthol lozenge] has pungency and a cooling effect which briefly relieves nasal discomfort. The pungency of menthol may stimulate vasoconstriction of the nasal blood vessels and this contributes to a brief decongestant action.

The sympathomimetic vasoconstrictors (decongestants) reduce nasal blood flow and symptoms of congestion, but these compounds have a number of adverse side-effects, including rebound hyperemia (rhinitis medicamentosa). The recommended dosing schedule is not to exceed one week of use, and preferably not more than three days.

It is a common experience that breathing cool air, for example at the seaside, will enhance the sense of fresh airflow in the nose. This effect has been demonstrated in the laboratory where subjects report a greater sense of nasal patency with lower nasal septum temperatures [Willatt et al. The role of the temperature of the nasal lining in the sensation of nasal patency. Clin. Otolaryngol. Allied Sci. 21, 519-523 (1996)]. Wei [U.S. Pat. No. 6,933,301. Aug. 23, 2005] proposed that a cooling agent, called icilin, administered into the nasal cavity may be useful for the relief of the symptoms of rhinitis, but this idea was not commercialized because of technical difficulties in formulating icilin for delivery into the nasal cavity.

Although physicians recommend intranasal steroids as the first medication of choice for the treatment of allergic rhinitis [Seidman et al., vide supra], patient adherence to effective use of intranasal steroids is variable [36% to 64%] In a survey conducted in 2012, only ⅓ of the patients with seasonal allergies used intranasal steroids for treatment [Fromer et al. J Family Practice Insights on allergic rhinitis from the patient perspective. 61: S16-22, 2012]. In controlled trials, however, the intranasal steroids give the most benefit to patients and, with the advent of over-the-counter approved intranasal steroids such as Nasacort®, Flonase®, and Rhinocort®, a relatively inexpensive and effective medication exists for the treatment of allergic rhinitis. Treatment of allergic rhinitis, and other forms of rhinitis, can be improved if there is a procedure to enhance patient acceptance of and adherence to an intranasally administered medication. Among the reasons for non-adherence are forgetfulness, the fear of side effects of intranasal steroids, bad taste or smell from the spray, alternative drugs (e.g. oral antihistamines), and the lack of immediate of symptomatic relief [Marple et al. Keys to successful management of patients with allergic rhinitis: focus on patient confidence, compliance, and satisfaction, Otolaryngol. Head. Neck Surg. 136, S107-24 (2007)].

BRIEF SUMMARY OF THE INVENTION

The preferred embodiments of this discovery (Formula 1 compounds) in an aqueous solution of 1 to 10 mg/mL and delivered at a volume of ~0.1 mL per nostril, will provide immediate (<2 min) relief of nasal irritation and congestion. The refreshing clearing of the nasal passages is felt upon spraying or the instillation of nose drops. This feature of immediate cooling and relief of nasal congestion will increase patient adherence/compliance to the use of the intranasal medication.

In one embodiment of the present invention, a combination composition is provided that comprises a cooling agent such as a 1-[Dialkyl-phosphinoyl]-alkane compound of Formula 1:

wherein each of $R_1$, $R_2$, is either isopropyl or sec-butyl and $R_3$ is a linear alkyl group of 6 to 9 carbons, and a topical medication for the treatment of nasal cavity disorders, such as an intranasal steroid, a intranasal antihistamine, a mast cell stabilizer, a sympathomimetic decongestant, a muscarinic antagonist, an antibacterial agent, an antifungal agent, or a saline solution for nasal irrigation.

Compounds of Formula 1 are an adjunct formulated into the combination composition. The composition is usefully delivered in a therapeutically effective amount as a solution onto the membranes of the nasal cavity, preferably by means of a spray, nose drops, or gel. A preferred embodiment of the compound of Formula 1 is represented by 1-[Diisopropyl-phosphinoyl]-octane [DIPA-1-8] or by 1-[Diisopropyl-phosphinoyl]-nonane [DIPA-1-9].

The preferred embodiments of the adjunct, DIPA-1-8 and DIPA-1-9 were selected because they impart an immediate, robust, and refreshing sensation to the nasal mucosa, without an effect on the nostril skin or pungency, and, at selected concentrations ranging from 0.01 to 1%, elicit a long-lasting enhancement of nasal refreshment. Upon instillation into the nostrils, the effects have immediate onset and are penetrating and refreshingly cool. Practice of this invention provides therapeutic medications that have improved acceptance and adherence by patients for the treatment of nasal cavity discomforts. Particularly for such sensations of nasal obstruction and nasal congestion caused, for example, by allergic rhinitis or rhinosinusitis.

An adjunct used in a medication is an additional substance or treatment used for increasing the efficacy or safety of the primary substance. The DAPA compounds relieve sensory discomfort in the nasal cavity. It is proposed that they be used as adjuncts with other pharmaceuticals for the nasal cavity site.

An adjunct such as DIPA-1-9 will facilitate "apparent" efficacy of another primary ingredient, and thereby improve patient satisfaction, compliance, and adherence to a dosage schedule. For example, DIPA-1-9 may be combined with an intranasal anti-inflammatory steroid such as triamcinolone acetonide in a formulation for rhinitis. The preparation may be more desirable than the anti-inflammatory steroid alone, which takes longer to act. Anti-inflammatory steroids used for intranasal applications include beclomethasone dipropionate, triamcinolone acetonide, budesonide, fluticasone propionate, mometasone furoate, ciclesonide, and fluticasone furoate. Other examples of intranasal drugs which may be combined with the DAPA compounds of this discovery include: antihistamines for intranasal applications such as olopatadine, azelastine, and levocabastine; sympathomimetic amine vasoconstrictors such as phenylephrine hydrochloride, oxymetazoline, naphazoline, and other imidazoline receptor agonists; ipratropium bromide which is an antimuscarinic agent used especially for rhinorrhea; sodium cromolyn which a mast cell stabilizer; and ketorolac, a non-steroidal anti-inflammatory agent; amphotericin B which is a anti-fungal agent; surfactants; and hypertonic and isotonic salne—all of which are used for topical medication of nasal-sinus membranes.

DETAILED DESCRIPTION OF THE INVENTION

Figure 1:
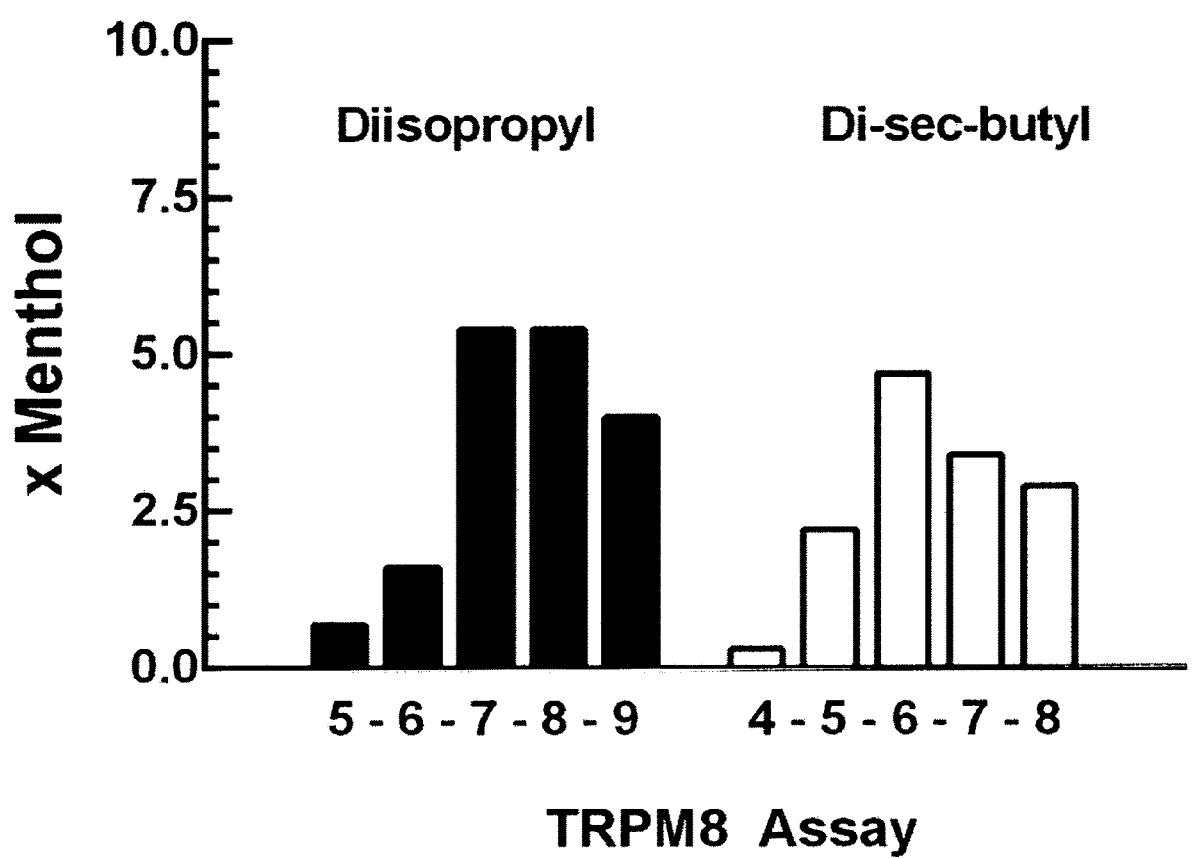
FIG. 1. is a graph of TRPM8 potency of Diisopropyl-phosphinoyl-alkane and Di-sec-butyl-phosphinoyl alkane analogs in the in vitro TRPM8 assay. Units are in comparison to I-menthol potency in the same assay. The numbers on the abscissa represent the number of carbons in one of the n-alkyl side-chain: that is, the 4-5-6-7-8-9 represents the butyl, pentyl, hexyl, heptyl, octyl, and nonyl group, respectively.

The nares, the pair of openings below the tip of the nose, are the entrances to the respiratory tract. The nasal passages serve as a conduit for inspired and expired air. When these passages are congested or obstructed, the condition is perceived as uncomfortable. The nasal cavity bony surfaces, including the sinuses, are lined by tissue called mucosa. This mucosa contains blood vessels, nerves, and small glands that secrete mucus and fluids into the nasal cavity. The respiratory epithelium which covers most of the nasal mucosa is only one cell layer thick and ciliated. The nasal mucosa is richly supplied by sensory nerves that detect pain, temperature, pressure and odor, and by motor nerves that regulate secretions and blood flow. The nasal mucosa humidifies and warms the inspired air, hence it receives a large blood flow and the cells maintain a high degree of metabolic activity. Inflammation of the nasal mucosa caused by allergy, infections, injury, or irritants and the like, will stimulate the mucosa to secrete fluids, to swell, and to obstruct. When the nasal membranes increase in volume, the area available through which air can pass is diminished, and therefore one experiences a sense of "stuffiness", resistance to inspiration, and a feeling of nasal obstruction and loss of patency. The nose can also become itchy and "runny" (rhinorrhea) and, as the fluids and discharges accumulate, the result is a feeling of congestion and discomfort.

The following descriptions give an over-view of some quantitative dimensions of nasal function. The normal air intake is about 10,000 liters per day and nasal secretions contribute about 30 ml of fluids to humidify each 1000 liters [300 mL per day is about the volume of a can of soda]. The relative humidity of dry air inhaled via the nose is about 60% when it goes past the nose, but it is only about 5% when the air is breathed through the mouth. The relative humidity of air in the bronchi is 100% at body temperature and this humidification, contributed by blood flow through the mucosa, is required to maintain ciliary activity and prevent epithelial changes in the bronchial mucosa. Desiccation of the bronchial surface for more than 2 to 3 hours can cause mucosal changes that result in thickening of secretions, irritation, and increased susceptibility to infection.

Abbreviations and Terminology

Adherence or Compliance—The two terms, used interchangeably, describe the degree to which a patient correctly follows professional advice on use of medication. Barriers to compliance include the clarity of instructions on proper use of the medication, poor patient understanding of treatment benefits, fear of and actual occurrence of side effects, the costs of the medicine, and the degree of understanding between patient and adviser. Frequently, a patient will listen to the advice of friends and use alternative medications such as vitamin supplements or herbal preparations if the prescribed medication does not work quickly. Adherence can be improved if there is immediate relief, by simplifying medication packaging, by providing effective reminders, by improving patient education, and/or by limiting the number of medications prescribed simultaneously. In this discovery, a pharmacological "boost" to a topical nasal cavity medication is provided by incorporating a cooling agent into the formulation. The goal is to give patient immediate relief of nasal congestion. The patient, by experiencing refreshed breathing may then adhere better to the treatment regimen, and let other drug actions, e.g. anti-inflammatory and anti-histaminergic become manifest. The term "adherence" now is preferred to "compliance" (by the WHO, American Pharmacists Association, and the NIH) because adherence implies the patient has greater freedom in cooperating with the health professional and is not just following didactic instructions. Both terms are accepted.

DAPA and DIPA compounds, DAPA and DIPA is the abbreviations for 1-[Dialkyl-phosphinoyl]-alkane and 1-[Diisopropyl-phosphinoyl]-alkane, respectively. 1-[Di-sec-butyl-phosphinoyl]-alkanes are also described in this application. An alternative name is 1-dialkylphosphorylalkanes. The third alkyl group in the molecule may be described by a number: hence, 4, 5, 6, 7, 8, 9, and 10 correspond to the butyl, pentyl, hexyl, heptyl, octyl, nonyl, and decanyl side chain, respectively. These alkanes are linear or "normal [n]" in configuration, with the phosphinoyl group attached to the primary, or "1-" position, of the carbon chain in the third sidechain. The syntheses of DIPA-5 to 7 and DIPA-9 to 10 were not previously reported but Siddall et al. [Simplified preparation of some trisubstituted phosphine oxides. J. Chemical Engineering Data 10: 303-305, 1965] reported the synthesis of DIPA 1-8 in 1965. The biological activities of the DIPA compounds applied to any organismic surfaces [e.g. nasal cavity] have not been reported prior to this discovery.

Nasal patency—is the subjective sensation of openness and smooth airflow in the nasal passages when breathing. Loss of patency may be reported as "nasal stuffiness" or "nasal blockage" and causes discomfort, and the subject may use mouth breathing which is undesirable because it desiccates the airway surfaces. Simple compression of the alar crease with the thumb and fore finger will cause the sense of impeded breathing. Nasal congestion implies excess fluids in the nasal passages. The term "nasal obstruction" is used more often when there is a physical, for example anatomical or structural, hindrance to airflow. Rhinitis, the inflammation of the membranes in the nasal cavity, is most often associated with nasal congestion and nasal obstruction. In the "empty nose syndrome" there are severe breathing discomforts, including loss of the sense of patency, but the symptoms can occur without rhinitis or physical evidence of change in airflow or gas exchange [Sozansky, J. Pathophysiology of empty nose syndrome. Laryngoscope 125, 70-74 (2015)].

Topical versus Systemic Administration—in the context of this discovery, topical administration is intranasal delivery of the drug ingredient onto the membranes of the nasal cavity directly via a spray, nose drops, or gel. Systemic administration is delivery of the drug to nasal membranes after passage into and distribution via the blood stream. Topical administration is safer than systemic in principle because the effective dose is much lower than the systemic effective dose due to less dilution in the body mass. To be effective, the topical active ingredient must not locally irritate the one-cell layer of the nasal epithelium.

Total Nasal Symptom Score (TNSS)—is a method, using a standardized questionnaire, to evaluate symptoms of nasal function in patients with allergic rhinitis. Scores are rated individually for: nasal congestion, runny nose, nasal itching, sneezing and difficult sleep, on a scale of none (0), mild (1), moderate (2), and severe (3) and the sum of the scores is the TNSS (min=0, max=15).

Cooling Agents and Nasal Cavity Physiology

Nasal cavity volume is not fixed by anatomy but fluctuates with the amount of blood in the venous capacitance vessels of the nose. In the nasal cycle, the side of the nose that is increased in volume is filled with the blood that is used to heat the incoming air. The blood supply to the nasal mucosa comes from five arteries. Both the internal and external carotid circulations contribute to the arterial supply of the nasal cavity. The anterior and posterior ethmoid arteries, branches of the ophthalmic artery, enter the nose after passing through the orbit and the lamina papyracea. The sphenopalatine artery, a terminal branch of the external carotid artery, enters the nose through the posterior lateral inferior wall. Additional blood supply comes from the greater palatine artery and the superior labial artery. Four of these vessels [the posterior ethmoid artery does not participate] anastomose and form a plexus of fenestrated capillaries some of which face the respiratory surface and are the major source of fluids and heat for humidifying and warming the air in the nasal cavity. Intranasal trigeminal fibers are distributed throughout the nasal cavity and are described as intraepithelial free nerve endings arising from A6 and C fibers of the nasopalatine and ethmoid branches of the trigeminal nerve. This neural network controls blood flow and secretions [Sahin-Yimaz A et al. Anatomy and physiology of the upper airway. Proc. Am. Thoracic Soc. 8:31-39, 2011].

It has been known for some time that an individual's perception of nasal patency [for example, on a visual analog scale of 0 to 10 with 0 for being clear and 10 for being blocked] is not readily correlated to objective measurements of nasal airflow or nasal cavity volume [Zhao, K. et al. Regional peak mucosal cooling predicts the perception of nasal patency. Laryngoscope 124, 589-595 (2014)]. Thus, physicians have been puzzled by the lack of consistent correlation between a patient's subjective complaints of congestion/blockage versus objective measurements, such as rhinomanometry for nasal airflow resistance, acoustic rhinometry for nasal cavity volume, and endoscopic examination of the nasal cavity. Without objective measurements of nasal function that relate to symptoms, medical treatment must rely the patient's opinions of patency for treatment success and this can lead to confusing outcomes, especially if surgery is contemplated.

Breathing cool air increases the sense of nasal patency. This is a fact of common experience, for example, breathing at the seaside. It has been shown in the laboratory when the inspired air temperature measured at the septum is kept at 25 to 35° C. there is a greater sense of patency at the lower temperature [Willatt et al., vide supra]. However, it is also well-known that cold and frigid air will evoke a "runny nose" or rhinorrhea, an event mediated by cholinergic nerves on serous glands of the nasal epithelium [Ostberg et al. Cold air induced rhinorrhea and high-dose ipratropium Arch. Otolaryngol. Head and Neck Surg. 113, 160-162 (1996)]. This condition has also been called a "skier's nose" and is quite common. Thus, cooling of the nasal cavity may increase secretions and exacerbate congestion. The negative effect of cooling on congestion is further shown by the fact that lowering the body temperature by immersion in cold water will cause vasodilation and increased nasal mucosal blood flow and hot water causes the nasal arteries to constrict [Lundqvist et al. Nasal reaction to changes in whole body temperature. Acta Otolaryngol. 113, 783-786 (1993)]. Thus, one cannot predict, ipso facto, that colder air temperatures will relieve congestion because cold causes rhinorrhea and increases nasal cavity volume.

The nasal afferents for detection of temperature are located in branches of the trigeminal nerve. The most likely receptor on the nerve endings mediating detection of coolness is the voltage-dependent cation channel called TRPM8, although a Grueneberg neuron receptor called CNGA3 may also participate [Mamasuew et al. The cyclic nucleotide-gated ion channel CNGA3 contributes to coolness-induced responses of Grueneberg ganglion neurons. Cell. Mol. Life Sci. 67, 1859-1869 (2010)]. Keh et al. [The menthol and cold sensation receptor TRPM8 in normal human nasal mucosa and rhinitis. Rhinology 49, 453-7 (2011)] have detected TRPM8 immunoreactivity in human nasal mucosa, closely associated with nerve fibers and blood vessels. The immunoreactive TRPM8 proteins in the nasal mucosa were not increased in patients with rhinitis. Keh et al. [2011] suggested that TRPM8 antagonists might have value in rhinitis. I propose here an opposite view; namely, TRPM8 agonists have beneficial effects in the nasal discomfort caused by rhinitis. In science there is often times confusion when one group says that the agonist will work, and another group advocates the antagonist. The data in this application clearly favor the agonists and not the antagonists.

The nerves and blood vessels of the nasal mucosa regulate the temperature and the humidification of air. The nerve endings participate in the inflammatory response by releasing transmitters, such as histamine, acetylcholine, CGRP, and substance P, that together with cells of the immune system control blood flow secretions. The sensors and effectors are highly concentrated in the anterior portion of the nose, at the anatomical juncture for the detection of the air temperature entering the nostrils. At first, one might hypothesize that cooling agents administered intranasally will inhibit the sensations of congestion by masking the signals of fullness and distension that accompanies nasal congestion. But this view is not correct because inhalation of menthol or inhalation of very cold air have limited beneficial effects on nasal stuffiness in clinical situations and menthol and cold stimulate rhinorrhea. Decreasing body temperature increases nasal mucosal blood flow [presumably to warm the incoming air].

Hypothesis on Mechanism of Drug Action

Without being bound by theory, I propose here a mechanism of drug action that might explain the findings in this invention. To go over the main observations:

- the delivery of microgram amounts of the DAPA compounds of this discovery to the anterior portion of the nasal cavity produces refreshing coolness and promotes an immediate sense of nasal patency.
- the benefit with one application of a DAPA compound for rhinitis is prolonged, lasting for 3+hr in some subjects
- DIPA analogs that produce intense cold, e.g. DIPA-1-7, are not as effective as compounds that produce mild cooling sensations, e.g. DIPA-1-9
- the selection of the active ingredient is based on the avoidance of excess cold sensation on nostril skin, and an optimal mild cooling of the nasal mucosa: hence the choice of active ingredient is not based on receptor potency, but on selective activity on nasal mucosa
- the onset of drug action to relieve congestion and to reduce nasal secretions occurs quickly, within minutes after application of the compound area, and the subjective description of the drug effect is "Amazing!" or "Miraculous!".
- this type of drug action has not been previously described for the treatment of nasal discomfort and is qualitatively distinct from the actions of intranasal glucocorticosteroids or antihistamines
- it is proposed that this pharmacological action of the preferred embodiments would be ideal as an adjunct in combination with other medications that act topically in the nasal cavity TRPM8 Agonists as Adjuncts for Nasal Cavity Medications.

Standard medications for certain forms of rhinitis (e.g. allergic rhinitis) are the intranasal corticosteroids and intranasal antihistamines. But these drugs do not work for rhinitis caused by the common cold or air pollutants. Anticholinergic drugs such as ipratropium and α-adrenergic sympathomimetic decongestants (e.g. phenyephrine, oxymetazoline, napthazoline) are used, but these drugs have limited efficacy. A combination of azelastine and mometasone has been introduced for allergic rhinitis (Dymista®), but generally combination drugs of nasal medications are infrequently used.

These criteria were defined as a desirable in an ideal active pharmacological ingredient [API] to be used as an adjunct in combination with a topical nasal cavity medications:

- the adjunct API should be easy to formulate with the nasal medication, e.g. a steroid. Ideally, the active ingredient should be water soluble at an effective therapeutic concentration at standard temperature and pressure
- the adjunct API should be selective for TRPM8 and not active at other TRP sensory channels such as TRPV1 and TRPA1
- the adjunct API when delivered should immediately refresh, provide a sense of cleansing, and increase the sense of nasal patency to a degree of therapeutic relevance
- the adjunct API should not over stimulate cold-sensing elements to cause "stinging cold" or cold rhinorrhea
- the adjunct API should be chemically stable in solution and not have odor or irritancy, and have an adequate safety margin
- the adjunct API should be potent, for example, at 0.1 to 5 mg/mL, and have a duration of drug action that is clinically meaningful
- the adjunct API should penetrate tissue barriers to reach targets in the presence of exudates in the nasal cavity
- the adjunct API should act in less than 5 min after topical delivery, thus favoring patient compliance and cooperation As shown in the studies described below, "ideal" API candidates were identified and comprise molecules of Formula 1; in particular, the preferred embodiment known as DIPA-1-8 and DIPA-1-9.

Pharmaceutical Adjunct and Rationale for Use in Rhinitis Medications

An adjunct is a substance added to a pharmaceutical to increase efficacy, adherence, or safety of the primary substance. In this discovery, a cooling agent is added to formulations to enhance adherence/compliance for use of a nasal cavity medication, especially a medication for rhinitis, and more particularly allergic rhinitis. The preferred embodiments are DAPA compounds that produce an immediate sense of refreshment to the nasal cavity and relieve nasal congestion and hence increase adherence.

Intranasal steroids, intranasal antihistamines, and decongestants are widely used in the treatment of allergic rhinitis. Marple et al. [vide supra] notes that there are at least 35 OTC medications and 28 prescription medications for allergic rhinitis. In a carefully conducted survey of 1200+ adults patients with seasonal allergic rhinitis, Marple et al. considered the factors for efficient management and adherence in the drug treatment of allergic rhinitis. Approximately 64% of such patients can forget to take their medications and one third consider their medications to be ineffective. Other factors for poor management and non-adherence include: dysphoric sedation and dry eyes and mouth in the first generation oral antihistamines; frequent dosing issues of second generation oral antihistamines and adequate management of plasma levels of drugs; the topical intranasal antihistamine azelastine has a bitter taste and work less well on the inflammatory aspects of rhinitis; intranasal decongestants run the risks of rebound hyperemia when used for more than 3 days; antimuscarinic agents work on rhinorrhea but do not seem to affect the sense of congestion, sneezing or itch; and sodium cromolyn has limited efficacy and slow onset. The intranasal corticosteroids are the best drug treatment for allergic rhinitis but earlier formulations had odor and affected smell and taste. Side effects such as epistaxis, pharyngitis, and nasal irritation were noted and some analogs had the systemic toxic effects of excess steroids, such as reduction in growth. Package inserts of intranasal steroids also warned of teratogenic effects in laboratory animals and possible increased risks of headaches. Amid such an abundance of confusing information, it is not surprising to a find a high rate of non-adherence.

Marple et al. in their comprehensive survey noted that patients ranked rapid, long-lasting, relief of symptoms as their highest desire in a medication (85 to 88% of the patients ranked these features as being important). Intranasal steroids can act as fast as 30 min but generally take a day or longer, up to one week, to be fully effective. Other priorities were: absence of side effects (e.g. drowsiness), low costs, easy to self-administer, compatibility with other medications, non-habit forming, dosing on an "as needed basis", "steroid free", and no after taste. An OTC preparation such as Nasacort® fufil virtually all of the desired qualities in an allergic rhinitis medication, except for being "steroid free" or having an immediate, rapid onset of action.

As shown in the Examples, an adjunct such as the preferred embodiment DIPA-1-9, administered into the nasal cavity will promote a sense of immediate clearing and relief of nasal congestion that lasts for hours. Thus, such an adjunct will facilitate "apparent" efficacy of another primary ingredient, and thereby improve patient satisfaction and adherence to a dosage schedule. For example, DIPA-1-9 may be combined with an intranasal anti-inflammatory steroid. The preparation may be more desirable than the anti-inflammatory steroid alone, which takes longer to act. Anti-inflammatory steroids used for intranasal applications include such beclomethasone dipropionate, triamcinolone acetonide, budesonide, fluticasone propionate, mometasone furoate, ciclesonide, and fluticasone furoate. Other examples of intranasal drugs which may be combined with the DAPA compounds of this discovery include: antihistamines for intranasal applications such as olopatadine, azelastine, and levocabastine; sympathomimetic amine vasoconstrictors such as phenylephrine hydrochloride, oxymetazoline, naphazoline, and other imidazoline receptor agonists, antimuscarinic agents such as ipratropium, a mast cell stabilizer such as sodium cromolyn and ketorolac which is approved for nasal administration. The adjunct DAPA compound can be also be used for combination medications such Dymista, which is a combination of mometasone furoate and azelastine chlorhydrate (Lulla and Malhotra. U.S. Pat. No. 8,937,057: Combination of azelastine and mometasone for nasal administration). The adjunct assisted medication may be useful for veterinarian as well as human therapy.

To my knowledge, the proposal to combine a fast-acting cooling agent with an intranasal steroid or an intranasal antihistamine to enhance patient acceptance and adherence to the use of nasal medication has not been previously described.

Study 1
1-[Dialkyl-phosphinoyl]-alkanes (DAPA)

The [Dialkyl-phosphinoyl]-alkanes [e.g. total number of carbons≤15] are solvent-like molecules that require only several [1 to 3] steps for synthesis. They are also known as trialkylphosphine oxides or 1-dialkylphophorylalkanes, but the term used here is [Dialkyl-phosphinoyl]-alkane [DAPA]. If two of the alkyl groups are isopropyl, the DAPA is abbreviated to DIPA [Diisopropyl-phosphinoyl-alkane].

Rowsell and Spring [Phosphine oxides having a physiological cooling effect. U.S. Pat. No. 4,070,496. Jan. 24, 1978], described a range of phosphine oxides which have a physiological cooling effect on skin and on the mucous membranes of the body, particularly the mouth, throat and gastrointestinal tract [columns 3 and 4 therein]. Ten (10) of the compounds shown in Rowsell have one isopropyl group. None of the compounds synthesized by Rowsell and Spring has two isopropyl groups or a n-nonane substituent. Rowsell and Spring considered the use of the trialkylphopshine oxides as a decongestant in combination with ephedrine, but is silent on the use of such compounds with intranasal steroids or intransal antihistamines, and on the questions of rapid onset of drug action and patient compliance in the use of nasal medications.

Siddall et al. [Simplified preparation of some trisubstituted phosphine oxides. J. Chemical Engineering Data 10: 303-305, 1965] reported the synthesis of 1-[Diisopropyl-phosphinoyl]-octane [DIPA-1-8]. No reports on any bioactivity of this or other diisopropyl-phosphinoyl-alkane compounds have previously been made.

Chemical Synthesis

In this discovery, DAPA compounds were synthesized and tested on:
  receptor activation assays
  in vivo animal assays
  human subjects with nasal discomfort.

From these studies four candidate API were identified that may have utility in the relief of nasal discomfort from irritants, allergens, and inflammation.

The DIPA compounds were prepared by the following general method: 100 mL (23.7 g, ~200 mmol) of isopropylmagnesium chloride (or sec-butylmagnesium chloride in the case of the di-sec-butyl derivatives) were obtained from Acros, as a 25% solution in tetrahydrofuran (THF) and placed under nitrogen in a 500 mL flask (with a stir bar). Diethylphosphite solution in THF (from Aldrich, D99234; 8.25 g, 60.6 mmol in 50 mL) was added drop-wise. After approximately 30 minutes, the reaction mixture warmed up to boiling. The reaction mixture was stirred for an extra 30 min, followed by a drop-wise addition of the appropriate n-alkyl iodide solution in THF (from TCI; 60 mmol in 20 mL). The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVap Buchi, bath temperature 40° C.). The light brown oil was distilled under high vacuum [0.5 mm Hg]. The final products, verified by mass as determined by mass spectrometry, were transparent liquids that were colorless or slightly pale yellow and had boiling points in the range of 120 to 130° C.

Several samples of DIPA-1-7 or DIPA-1-8 were sent for detailed analysis by GC-MS (NCE Corporation, Pleasanton, Calif., USA, www.nceanalytical.com). Analysis was conducted on an Agilent GC/MS system 6890/5973 equipped with a TraceGold TG-624 column, with helium as the carrier gas [flow rate: 1.6 mL/min] and the injector port set at 220° C. [split ratio 50:1, temperature program: 100 to 240° C.]. The TIC [total ion chromatogram] showed the main components as having a retention time of 18 to 19 min, with the detected peaks accounting for 97.2% of the total area. Similar results of 97 to 99% purity were obtained with other samples. When gas chromatography [equipped with a flame ionization detector (Dong Wha Corporation, Seoul, Korea)] was used as the analytical system, synthesized compounds were also found to be 97 to 99% chromatographically pure.

The following compounds were prepared by this method wherein Table 1A and Table 1B compounds are embodiments of the invention.

TABLE 1A

Chemical structures of diisopropyl-analogs.

| Code | Chemical Name | Chemical Structure |
|---|---|---|
| DIPA-1-5 | 1-[Diisopropyl-phosphinoyl]-pentane | 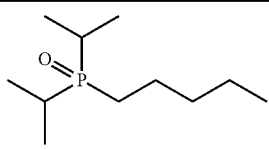 |

TABLE 1A-continued

Chemical structures of diisopropyl-analogs.

| Code | Chemical Name | Chemical Structure |
|---|---|---|
| DIPA-1-6 | 1-[Diisopropyl-phosphinoyl]-hexane | 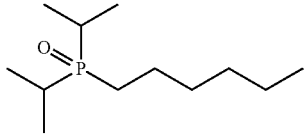 |
| DIPA-1-7 | 1-[Diisopropyl-phosphinoyl]-heptane | 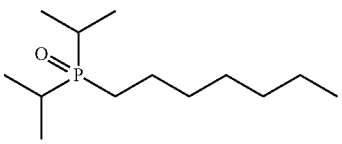 |
| DIPA-1-8 | 1-[Diisopropyl-phosphinoyl]-octane | 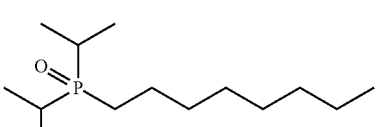 |
| DIPA-1-9 | 1-[Diisopropyl-phosphinoyl]-nonane | 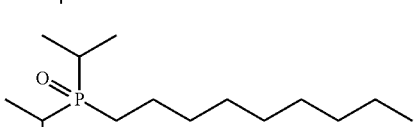 |

TABLE 1B

Chemical structures of di-sec-butyl-analogs.

| Code | Chemical Name | Chemical Structure |
|---|---|---|
| 2-4 | 1-[Di-sec-butyl-phosphinoyl]-butane | 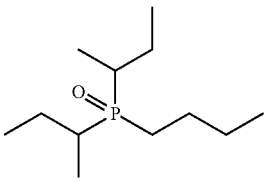 |
| 2-5 | 1-[Di-sec-butyl-phosphinoyl]-pentane | 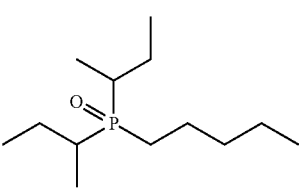 |
| 2-6 | 1-[Di-sec-butyl-phosphinoyl]-hexane | 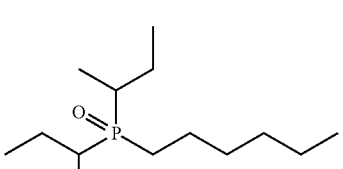 |

TABLE 1B-continued

Chemical structures of di-sec-butyl-analogs.

| Code | Chemical Name | Chemical Structure |
|---|---|---|
| 2-7 | 1-[Di-sec-butyl-phosphinoyl]-heptane | 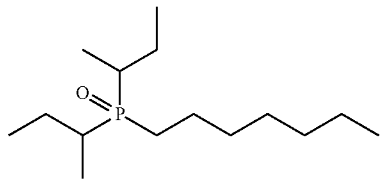 [SMILES: CCCCCCCP(=O)(C(C)CC)C(C)CC] |
| 2-8 | 1-[Di-sec-butyl-phosphinoyl]-octane | 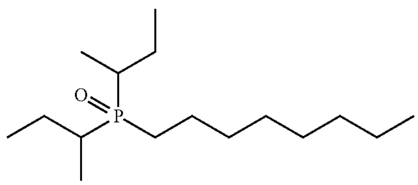 [SMILES: CCCCCCCCP(=O)(C(C)CC)C(C)CC] |
| 3-1 | 1-[Diisobutyl-phosphinoyl]-pentane | 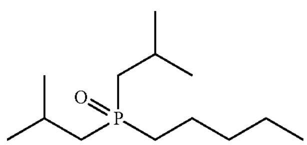 |
| 3-2 | 1-[Di-sec-butyl-phosphinoyl]-3-methyl-butane | 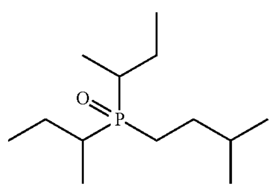 |

General Observations on DAPA Compounds

DAPA compounds are colorless liquids with a density less than water [0.7 to 0.8 g/cc]. They are generally soluble in water or saline at up to 20 mg/mL, or for the compounds with greater than or equal to 16 carbon atoms, a homogeneous emulsion of very fine droplets. When DAPA compounds are applied to the facial skin as an aqueous solution at 5 to 10 mg/mL there is no irritation or blanching. For certain analogs, contacting the facial skin with a solution at a concentration of 5-20 mg/mL produce a sensation of strong cooling within 1 min especially when applied to periorbital skin. The effects are strong on non-keratinzing tissues such as the lining of the upper digestive tract and the ocular margins. The effects of these compounds after intranasal instillation have not been reported in the literature.

The pharmacological effects of DIPA-1-8 and DIPA-1-9 are clearly differentiated from the sympathomimetic decongestants. DIPA-1-9 does not cause blanching of the skin or reduce redness from the blood vessels of the eyelids which are classical signs of α-adrenergic sympathomimetic activity. These compounds have a mild cooling action on human nasal mucosa, an effect that is not seen with sympathomimetic decongestants. Sympathomimetic agonists such as clonidine do not interact do not activate TRPM8 [Bavencoffe, A. et al. The transient receptor potential channel TRPM8 is inhibited via the α2A adrenoreceptor signaling pathway. J. Biol. Chem. 285, 9410-9419 (2010)]. The long durations of action of DIPA-1-8 and DIPA-1-9 are also not seen with the standard sympathomimetic decongestants.

Note that the diisopropyl groups of the DIPA compounds of this invention do not have a chiral center but each of the sec-butyl groups in compounds of the Di-sec-butyl-phosphinoyl series has a chiral centre, and that each chiral centre may independently be in the (R) or (S) configuration. As a consequence, a compound such as 2-6 has four possible stereoisomers: two optically active stereoisomers (i.e., R,R and S,S), and two optically inactive meso forms (i.e., R,S and S,R). Unless otherwise indicated, a reference to Di-sec-butyl-phosphinoyl compounds is intended to be reference to any one of the four stereoisomers, and any mixture of any two or more of the four stereoisomers. The absence of stereoisomers in the DIPA compounds is an advantage in drug development over molecules containing sec-butyl groups because current regulations often require that each enantiomer be either synthesized or isolated separately and then individually evaluated for toxicological activities.

The effects of diisopropyl versus the di-sec-butyl congeners were strikingly different in laboratory rats when given by the perioral or topical routes. [Table 3]. Perioral or topical application of DIPA analogs [DIPA-1-5, DIPA-1-6, DIPA-1-7] elicits vigorous shaking in the whole animal, but this effect is hardly seen with the di-sec-butyl congeners. This is because DIPA-1-5, DIPA-1-6, and DIPA-1-7 are able to penetrate the membrane barriers in the gut and keratinized skin. When given intravenously, the di-sec-butyl analogs are active.

Additional Terminology Used

Compositions: One aspect of the present discovery pertains to a composition (e.g., a pharmaceutical composition) comprising a DAPA compound, as described herein, and a pharmaceutically acceptable carrier, diluent, or excipient. Another aspect of the present discovery pertains to a method of preparing a composition (e.g., a pharmaceutical composition) comprising mixing a DAPA compound, as described herein, and a pharmaceutically acceptable aqueous solution. In one embodiment, the composition comprises the DAPA compound as an aqueous solution at a concentration of 0.5-20 mg/mL. The composition may be provided with suitable packaging and/or in a suitable container. For example, the composition may be provided as a manually activated sprayer or as nose drops carrying a DAPA compound or a composition comprising a DAPA compound.

Discomfort of the Nasal Cavity: In one embodiment (e.g., of use in methods of therapy, of use in the manufacture of medicaments, of methods of treatment), the treatment is treatment of sensory discomfort. In a second aspect of treatment, the treatment is to provide immediate symptomatic relief of nasal congestion, and thus to increase patient awareness and adherence to use of the medication. In the second aspect, in which the combination embodiment has a faster onset of action, the treatment has prophylactic and therapeutic actions.

The term "sensory discomfort", as used herein, relates to irritation, itch, pain, or other dysesthesias (abnormal sensations; such as "stuffiness", congestion, obstruction, burning sensations, or feeling the presence of a foreign body, or pins and needles) from the nasal cavity surfaces. The term implies activation of nociceptors located on sensory nerve endings of the body. Nociceptors are stimulated, for example, by high or low temperatures, mechanical pressure, chemicals (e.g., capsaicin, acidity, pollutants, etc.), injury, inflammation, and inflammatory mediators. A compound, such as DIPA-1-8 or DIPA-1-9, that decreases sensory discomfort, can be termed an anti-nociceptive agent.

In one embodiment, the treatment is treatment of rhinitis and sinusitis. In one embodiment, the treatment is treatment of the symptoms of the "empty nose syndrome". In one embodiment, the treatment is treatment of nasal irritation from air pollutants. In one embodiment, the treatment is treatment of heat discomfort. In one embodiment, the treatment is treatment of rhinosinusitis. In one embodiment, the treatment is to refresh breathing sensations, to reduce snoring, and to reduce sleep apnea. In one embodiment, the treatment is treatment of allergic rhinitis. In one embodiment, the treatment is treatment is to convey a sense of refreshment to breathing in a human which can enhance meditative exercises such as yoga.

Treatment: The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment." Treatment to enhance the basal levels of cognitive awareness of the medication for the purposes of increasing adherence to the use of the medication is also included.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Routes of Administration: The term "topical application", as used herein, refers to delivery onto surfaces of the nasal cavity in contact with air.

Subject/Patient may be a mammal, for example, a canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orang-utang, gibbon), or a human. In one preferred embodiment, the subject/patient is a human.

Dosage: The dose and dosing regimen can be on an "as needed basis" or once or twice daily, depending on the severity of the condition being treated. Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Delivery Systems and Tissue Targets

The targets for drug delivery are the non-keratinizng stratified epithelium, such as the respiratory epithelium, covering the nasal cavity and the paranasal sinuses. Treatment is focused on the inflammatory processes underlying the rhinitis as the best way to treat disorders of the nasal cavity.

The delivery of the DAPA compounds can be achieved with the compound dissolved in purified water or isotonic saline or phosphate buffered saline. For a liquid vehicle, a preferred concentration of the DAPA compound is in the range of 0.5 to 10 mg/mL. A preferred amount of the DAPA compound delivered at the site of application is 0.5 to 5 mg.

Little is directly known about the neurophysiology of tissue targets in the nasal cavity [except for olfaction]. The surface is innervated by a branch of the trigeminal nerve. The terminology for describing the sensations of the nasal surfaces is not standardized. For example, menthol lozenges cool the nasopharynx, but it is not clear if it cools the turbinates. Inhaled menthol vapors are pungent, but it is not clear if these sensations can be described as cool or cold. Breathing frigid air causes sting and rhinorrhea. Only breathing cool air, for example, at the seaside convey the right degree of coolness and the sense of patency. This sensation is pleasurable, but the exact air temperature and humidity for capturing this sensation have not been defined.

There is a general view that "TRP-" ion channel receptors (A1, M8, and V1 to 4) are the principal physiological elements for physiological temperature detection. The TRPM8 receptor is the one that responds to sensory/cooling agents such as menthol and icilin [McKemy et al. Identification of a cold receptor reveals a general role for TRP channels in thermosensation, Nature, 416, 52-58, 2002]. TRPM8 is a protein with 1104-amino acid residues and has six transmembrane domains. Activation of this receptor by lowering ambient temperature results in opening of pores of transmembrane loop and non-specific cation entry into the cell. Depolarization of TRPM8 receptors on sensory neurons may then transmit signals to the central nervous system primarily via $A\delta$ (and some C) fibres.

While this concept for the role of TRPM8 in sensory physiology may be valid for detecting physical changes in temperature, the interpretation of the sensory effects of chemical agents such as menthol and icilin are more complex. Menthol not only stimulates TRPM8 in vitro, but also TRPV3, a receptor associated with warmth and glycinergic transmission [Macpherson et al. More than cool: promiscuous relationships of menthol and other sensory compounds. Mol Cell Neurosci 32:335-343, 2006: Sherkheli et al., Supercooling agent icilin blocks a warmth-sensing ion channel TRPV3, Scientific World Journal, 2012: 982725, 2012: Cho et al. TRPA1-like channels enhance glycinergic transmission in medullary dorsal horn neurons. J Neurochem 122:691-701, 2012]. Thus, menthol and icilin are called "promiscuous" agents and are not selective for one receptor protein.

The Applicant has screened a large database of cooling agents for sensory effects on the skin [keratinizing] and the ocular rim [non-keratinizing] and found that there are distinct responsive elements in the two types of epithelia [Wei. Sensory/cooling agents for skin discomfort. Journal Skin Barrier Research 14: 5-12, 2012].

The epithelia of the nares and the anterior nasal vestibule are keratinizing, but then transitions to respiratory epithelium [non-keratinizing]. When one examines the structure-activity relationships (SAR) of the DAPA compounds [Formula 1] on keratinized skin, it is noted that when $R_1=R_2$=isopropyl and $R_3$=n-hexyl ($C_6$) or n-heptyl ($C_7$), then strong penetrating cooling is observed. Cooling of long duration is obtained on non-keratinizing epithelia with $R_3$=n-octyl (CO and n-nonyl ($C_6$). However, when $R_1=R_2$=sec-butyl dynamic cooling is observed when $R_3$=n-pentyl to n-heptyl ($C_5$ to $C_7$). Thus, there are subtle differences among the compounds embraced by Formula 1.

Shaking behavior is a rapid alternating contraction of the supination and pronation muscles about the spinal axis, and is readily observed and counted. Fur-coated and feathered animals—when wet and cold—shake, like a wet dog [Dickerson et al., Wet mammals shake at tuned frequencies to dry. J. Royal Society, Interface 9, 3208-3218, 2012; Ortega-Jimenez, V. M. et al. Aerial shaking performance of wet Anna's hummingbirds. J. Royal Society, Interface 9, 1093-9, 2012; Wei, Pharmacological aspects of shaking behavior produced by TRH, AG-3-5, and morphine withdrawal, Federation Proc. 40: 1491-1496, 1981].

"Wet-dog shaking" has been studied in detail in animals. Rats can shake their head, the upper torso, or the shaking can be sufficiently violent to affect the whole body and make the animal lose its balance. The purpose or survival value of shaking to fur-coated and feathered organisms is to remove water droplets trapped on or near the skin. Removal of the water droplets on or near the skin by shaking reduces the organism's need to expend energy to remove the water by evaporation. The likely equivalent behaviour to shaking in humans is shivering, a condition caused by generalized sensations of coolness/cold. Human subjects recovering from the deep hypothermia of anaesthesia manifest vigorous shaking; a condition called post-anaesthetic shivering.

For the DAPA compounds the shaking frequency seen after intravenous injection is a good approximation of the compound's potency for producing cold when administered into the nasal cavity surfaces.

Test compounds were also evaluated on receptor assays: on cloned hTRPM8 channel (encoded by the human TRPM8 gene, expressed in CHO cells) using a Fluo-8 calcium kit and a Fluorescence Imaging Plate Reader (FLIP-RTETRA™) instrument. The specificity of the test compounds were examined on TRPV1 channels (human TRPV1 gene expressed in HEK293 cells) and TRPA1 channels (human TRPA1 gene expressed in CHO cells). ChanTest Corporation, 14656 Neo Parkway, Cleveland, Ohio 44128, USA, was the contractor for these tests.

Selection of Active Ingredient

Ideally, an active pharmaceutical ingredient (API) formulated for delivery to the nasal epithelium should be chemically stable, non-toxic, and sufficiently long-acting and potent to activate the mechanisms that result in a sense of refreshed breathing and a reduction of nasal discomfort. The API should be dissolved and evenly dispersed in a composition so that during manufacture the formulation maintains a constant concentration. The final product should meet standards of cleanliness and sterility. For purposes of formulation, the API can be a liquid at standard conditions of temperature and pressure (STP) and that is evenly dissolved in aqueous solutions at neutral pH and/or isotonicity. Sterility of the final product can be optimally achieved by using purified reagents and filtration through micropore filters, heating, or irradiation. Standard excipients, such as preservatives, may be added to optimize the formulations, but the important ingredients should be preferably soluble in aqueous media such as purified water, isotonic saline, or phosphate buffers.

For a given individual, the perceived sensation is a function of the particular cooling agent, the dose, the vehicle used to carry the cooling agent, the method of topical delivery, and the nature of the target surfaces. The Applicant has screened a number of candidate compounds, including diverse compounds such as p-menthane carboxamides and icilin [Wei, 2012 vide supra]. The studies here identify DIPA-1-8, DIPA-1-9, 2-6 and 2-7 as having the preferred desired properties of an ideal API for the nasal cavity epithelium to refresh, to reduce rhinorrhea, to be compatible with formulations of an intranasal steroid or intranasal antihistamine, and to enhance patient adherence to use of a topical intranasal medication. These analogs are selected because they produce mild cooling on nasal mucosa and do not produce excessive cooling on nasal skin.

A key factor to the successful management of nasal discomfort is the water-solubility of the active ingredient for delivery to the nasal mucosa. A water-soluble API has tremendous advantages for ease and for homogeneity of delivery to the target. If a chemical is not soluble in water, solvents and excipients must be used. Then the solvent or matrix used has to be free of unpleasant effects on the nasal mucosa.

The applicant has screened a number of water soluble and water insoluble compounds and the results are described in Case Study 5. For water soluble compounds such as CPS-030 [WS-30] [U.S. Ser. No. 13/261,061], (L)-Monomenthane-3yl carbonate [RightCool™ monomenthyl glutarate], and 3-(1-Methoxy)propane-1,2-diol [Cooler 10] were tested. The goal was to determine if such compounds can accelerate the sense of patency. It was found that CPS-030 at 5 mg/mL produced immediate sensations of coolness, but this was also felt on the skin of the nostrils, and there was a sense of wetness. Monomenthyl glutarate and Cooler 10, which are water soluble, were not active at 8 mg/mL Thus, CPS-030 could potentially be used as an enhancer of the DAPA compounds, to inform the patient that a drug had been delivered to the nose.

Water insoluble compounds may be useful for chronic rhinosinusitis or the "empty nose syndrome" because these disease conditions are long-lasting. With the correct formulations, e.g. milling and suspension into very fine particles or the incorporation of these compounds into gels, these water insoluble compounds, based on their chemical structure and reported pharmacological properties, are reasonable choices for prolonging duration of action if combined with DAPA compounds. These are some candidate compound: icilin; CPS-125 [2-isopropyl-5-methyl-cyclohexanecarboxylic acid [4-(pyrimidin-2-ylsulfamoyl)-phenyl]-amide]; CPS-195 [,2-Isopropyl-5-methyl-cyclohexanecarboxylic acid [2'-hydroxy-2'-(3"-hydroxy-phenyl)-ethyl]-N-methyl-amide]; Ax-8 [((1R,2S,5R)-2-isopropyl-5-methyl-cyclohexane-carbonyl)-amino]-acetic acid isopropyl ester; Ax-10 (R)-2-[((1R,2S,5R)-2-isopropyl-5-methyl-cyclohexanecarbonyl)-amino]-propionic acid isopropyl ester; (1R,2S,5R)-2-isopropyl-5-methyl-N-(2-(pyridin-2-yl)-ethyl-cyclohexanecarbox-amide; (1R,2S,5R)—N-(4-(cyanomethyl)-phenyl)-2-isopropyl-5-methylcyclohexyl carboxamide, and "M8-Ag" (4-[5-(4-chlorophenyl)-4-phenyl-4H-1,2,4-triazol-3-yl]morpholine [Patel, R. Anti-hyperalgesic effects of a novel TRPM8 agonist in neuropathic rats: A comparison with topical menthol. Pain 155, 2097-107 (2014)].

To summarize the design concepts that lead to the selection of the API, the delivery system, and the site of delivery, as being suitable for the practice of the discovery:

DAPA compounds were identified that were soluble in water at up to 20 mg/mL. These compounds are stable to heat, and exerted a potent therapeutic effect on nasal discomfort and inflammation at applied concentration of 1 to 10 mg/mL. In animal studies, tachyphylaxis does not develop to repeat applications.

The receptor target for DAPA compounds was ascertained in in vitro studies. The lead candidate was selective for TRPM8 and not for TRPV1 or TRPA1.

The biological activity of DAPA compounds was defined in an animal model of "wet-dog shakes". The perioral, topical/dermal, and intravenous activates were compared, and the selective differentiation of diisopropyl analogs from di-sec-butyl analogs was established.

In volunteers with rhinitis and nasal discomfort, the efficacy of four compounds for reducing nasal discomfort and rhinitis was established.

Compounds that produced strong cold on keratinized nasal skin, e.g. DIPA1-7, were considered less desirable than compounds that mildly refreshed the nasal mucosa [a non-keratinizing surface]. DIPA1-8 and DIPA1-9, were chosen as lead candidates.

Tests in human volunteers showed that four compounds, especially DIPA-1-8 and DIPA-1-9, were effective for relieving sensory discomfort from rhinitis and nasal pollutants. In normal subjects, there was enhanced refreshed breathing.

Tests of combinations of the DAPA compounds of the preferred embodiments showed that these compounds were compatible with some standard formulations of intranasal steroids and intranasal antihistamines.

Administration of these combinations showed that the combination was the preferred nasal medication and increased patient adherence to a dosage regimen.

Study 2
Results of TRPM8, TRPA1, and TRPV1 Receptor Assays:

The in vitro effects of test compounds were evaluated on cloned hTRPM8 channel (encoded by the human TRPM8 gene, expressed in CHO cells) using a Fluo-8 calcium kit and a Fluorescence Imaging Plate Reader (FLIP-RTETRA™) instrument. To examine the specificity of the test compounds, further tests were conducted on TRPV1 channels (human TRPV1 gene expressed in HEK293 cells) and TRPA1 channels (human TRPA1 gene expressed in CHO cells). The assays were conducted by ChanTest Corporation, 14656 Neo Parkway, Cleveland, Ohio 44128, USA.

Test compounds and positive control solutions were prepared by diluting stock solutions in a HEPES-buffered physiological saline (HBPS) solution. The test compound and control formulations were loaded in polypropylene or glass-lined 384-well plates, and placed into the FLIPR instrument (Molecular Devices Corporation, Union City, Calif., USA). The test compounds were evaluated at 4 or 8 concentrations with n=4 replicates per determination. The positive control reference compound was L-menthol, a known TRPM8 agonist. The test cells were Chinese Hamster Ovary (CHO) cells stably transfected with human TRPM8 cDNAs.

For FLIPRTETRA™ assay, cells were plated in 384-well black wall, flat clear-bottom microtiter plates (Type: BD Biocoat Poly-D-Lysine Multiwell Cell Culture Plate) at approximately 30,000 cells per well. Cells were incubated at 37° C. overnight to reach a near confluent monolayer appropriate for use in a fluorescence assay. The test procedure was to remove the growth media and to add 40 μL of HBPS containing Fluo-8 for 30 minutes at 37° C. 10 μL of test compound, vehicle, or control solutions in HBPS were added to each well and read for 4 minutes.

Concentration-response data were analyzed via the FLIPR Control software that is supplied with the FLIPR System (MDS-AT) and fitted to a Hill equation of the following form:

$$\text{RESPONSE} = \text{Base} + \frac{\text{Max} - \text{Base}}{1 + \left(\frac{xhalf}{x}\right)^{rate}}$$

where: "Base" is the response at low concentrations of test compound; "Max" is the maximum response at high concentrations; "xhalf" is the $EC_{50}$, the concentration of test compound producing half-maximal activation; and "rate" is the Hill coefficient. Nonlinear least squares fits were made assuming a simple one-to-one binding model. The 95% Confidence Interval was obtained using the Graph Pad Prism 6 software.

Of the 12 compounds tested, all showed full efficacy on the TRPM8 receptor, i.e., at higher tested concentrations there was ~100% stimulation of calcium entry, and the data fitted a sigmoidal dose-response curve. The results for 10 of the compounds of this invention are illustrated in FIG. 1.

FIG. 1 is a graph of TRPM8 potency of Diisopropylphosphinoyl and Di-sec-butyl phosphinoyl alkane analogs in the in vitro TRPM8 assay. Units are in comparison to l-menthol potency in the same assay. The numbers on the abscissa represent the number of carbons in one of the n-alkyl side-chain: namely, the 4-5-6-7-8-9 represents the butyl, pentyl, hexyl, heptyl, octyl, and nonyl group, respectively.

The $EC_{50}$ of the more potent compounds (DIPA-1-7, DIPA-1-8, DIPA-1-9, 2-5, 2-6, 2-7, 2-8) fell within a narrow range with overlapping 95% Confidence Intervals. [Table 2] The potency of DIPA-1-7 and DIPA-1-8 are similar and significantly greater than the potencies of DIPA-1-5 and DIPA-1-6. By contrast the structural modifications of comparative compounds 3-1 and 3-2 resulted in a significant loss of bioactivity. DIPA-1-10 was synthesized at a later time and tested by David Andersson of King's College, London, U.K. It was found to be 2.4× less active than DIPA-1-9 [or 1.7× menthol on Table 2]. The data for DIPA-1-10 is not included in the Table 2 because it was obtained under different assay conditions.

To examine the specificity of the test compounds, further studies were conducted on TRPV1 channels (human TRPV1 gene expressed in HEK293 cells) and TRPA1 channels (human TRPA1 gene expressed in CHO cells). The test cells were Chinese Hamster Ovary (CHO) cells or Human Embyronic Kidney (HEK) 293 cells transfected with human TRPV1 or TRPA1 cDNAs. The positive control reference compound was capsaicin (a known TRPV1 agonist) or mustard oil (a known TRPA1 agonist). DIPA-1-7 and DIPA-1-8 did not exhibit any agonist on antagonist activity on TRPA1 channels at maximum tested concentrations of 100 µM. The results for DIPA-1-8 are shown in FIG. 2.

Figure 2:
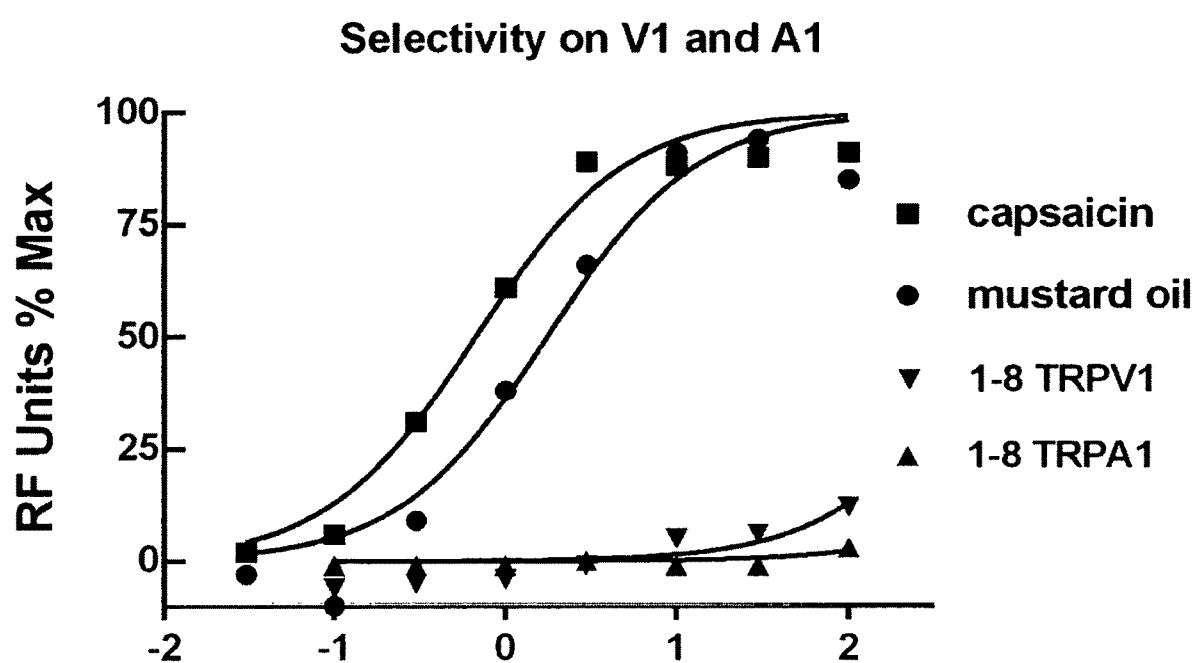
FIG. 2. is a graph showing the lack of agonist activity of DIPA-1-8 in cells transfected with TRPV1 or TRPA1 plasmids. The positive controls capsaicin and mustard oil for TRPV1 and TRPA1 are active, respectively, but DIPA-1-8 is not active in these TRPV1 or TRPA1 transfected cells. The ordinate is given in Relative Fluorescence Units % of maximum, which measure calcium entry into the transfected cells and the abscissa is the logarithm of the concentration of the test compound.

FIG. 2 shows the lack of agonist activity of DIPA-1-8 in cells transfected with TRPV1 or TRPA1 plasmids. The positive controls capsaicin and mustard oil for TRPV1 and TRPA1 are active, but DIPA-1-8 is not. The ordinate is given in Relative Fluorescence Units; % of maximum, which measure calcium entry into the transfected cells and the abscissa is the logarithm of the concentration of the test compound. DIPA-1-8 was also devoid of antagonist activity against TRPV1 or TRPA1.

The $EC_{50}$ values do not give information on the quality of the heat abstraction sensation in the nasal cavity, on the duration of action, or on the accessibility [distribution] of the molecule to tissue targets such as the nasal mucosa. The $EC_{50}$, however, gives guidance on the relative potencies of the different analogs. Of special importance is the differentiation of the drug effect on the keratinized epithelia of the nose [nostril skin and vestibule] versus the non-keratinizing epithelia of the nasal mucosa. The use of the aqueous solution on the swab makes the drug available to all epithelia. The identification of agents that are optimized for the nasal mucosa requires bioassays that directly address these questions. Part of the discovery process here is the recognition that stimulation of cold receptors on the keratinized surfaces is not desirable, whereas stimulation of the mucosal receptors gives the desired drug effect. Both responses are likely to be mediated by the TRPM8 receptor protein and correlated to the $EC_{50}$. The presence of 15 to 16 carbons in molecules of Formula 1 appear to optimize the localization and distribution of the drug candidate to the nasal mucosa.

TABLE 2

$EC_{50}$ and relative potency of compounds on TRPM8..

| Code | $EC_{50}$ µM | 95% Confidence Interval | Relative Potency |
|---|---|---|---|
| Menthol | 3.8 | 2.5 to 5.6 | 1.0 |
| DIPA-1-5 | 5.6 | 4.4 to 7.2 | 0.7 |
| DIPA-1-6 | 2.4 | 1.5 to 4.0 | 1.6 |
| DIPA-1-7 | 0.7 | 0.5 to 1.0 | 5.4 |
| DIPA-1-8 | 0.7 | 0.5 to 1.0 | 5.4 |
| DIPA-1-9 | 0.9 | 0.4 to 2.5 | 4.0 |
| 2-4 | 14.5 | 7 to 29 | 0.3 |
| 2-5 | 1.7 | 1.0 to 2.9 | 2.2 |
| 2-6 | 0.8 | 0.5 to 1.3 | 4.7 |
| 2-7 | 1.1 | 0.6 to 2.3 | 3.4 |
| 2-8 | 1.3 | 0.7 to 2.3 | 2.9 |
| 3-1 | 24 | 8 to 76 | 0.2 |
| 3-2 | 4.2 | 1.6 to 10.8 | 0.9 |

Study 3
Activity in Laboratory Rat: Perioral, Topical and Intravenous Delivery

To get a better idea on the in vivo activity of these DAPA compounds further studies were conducted on the laboratory rat after administration of the test compounds by three different routes: intravenous, perioral, and topical. Variation on the routes of administration provides information on the ability of the molecule to cross membrane barriers.

Fur-coated and feathered animals—when wet and cold—shake, like a wet dog (see, e.g., Dickerson et al., 2012; Ortega-Jimenez et al., 2012; Wei, 1981). These shakes are rapid alternating contractions of the supination and pronation muscles about the spinal axis, and can be readily observed and counted. "Wet-dog shaking" has been studied in detail in animals and this behavior is interpreted to have survival value because shaking, by removing the water off t skin, reduces the need to expend evaporative energy to remove wetness. The triggering sensation for shaking is thus having water trapped in between hair follicles or feathers. Humans have little hair on skin and do not shake. The likely equivalent behavior to shaking in humans is shivering, a condition caused by generalized sensations of coolness/cold and wetness.

Drug-induced shaking in animals has been reviewed (see, e.g., Wei, 1981). Under the right conditions, drug-induced shaking can be observed in the pentobarbital-anesthetized rat, enhanced by hypothermia and cold, and inhibited by elevating body temperature.

In experiments conducted here, test compounds were evaluated for "wet-dog shaking" as a model of cooling sensation. Using a standardized procedure, test compounds were compared in their ability to stimulate the shaking response by perioral administration, by topical delivery to the abdominal skin, and by intravenous administration through a cannulated femoral vein.

Perioral. Test compounds were dissolved in saline and administered by oral gavage to pentobarbital-anesthetized male albino rats at 20 mg/kg at a volume of 0.1 mL/100 g body weight [n=3 to 4 rats per compound]. Shaking was counted over a 40 min period and recorded at 10-min intervals. The results are shown in Table 3.

Three of the four "diisopropyl" compounds caused vigorous shaking. The "di-sec-butyl" compounds were relatively inactive, except 2-5 which elicited an average of 4 shakes in the 40 min observation period. By contrast, DIPA-1-5, DIPA-1-6, and DIPA-1-7 produced an average shaking frequency of 86, 56, and 36 shakes, respectively. The strong activity of DIPA-1-5 was unusual. Applied to the skin, DIPA-1-5 has a refreshing cooling sensation, but the duration of action of only about 30 min was significantly less than that for DIPA-1-6 and DIPA-1-7. It is possible that its smaller molecular size facilitates absorption and allows greater access to systemic receptors, and therefore more shaking.

The relationship of the shake response to temperature sensation was further studied [in pentobarbital-anesthetized rats]. After injection of the sodium pentobarbital anesthetic, rectal temperature drops, and reaches approximately 35° C. in about 10 min. This hypothermia can be reversed by placing the animal on a heated surface and body temperature maintained at 38° C. DIPA-1-7 20 mg/kg perioral elicited 36±5 shakes (n=6) in the anesthetized rat, but in the heated animals, the shaking frequency was significantly reduced to 5±2 shakes (n=6) [P<0.001]. The reduction of shaking frequency by ⅔ under heat indicated that the shake response was linked to cold sensations and shivering.

Topical.

Shaking is an excellent indicator of in vivo effect. Methods were developed to determine if shaking was seen after topical application of DAPA compounds. The abdominal skin of the pentobarbital-anesthetized rat was shaved and 20 μL of the pure unadulterated DIPA chemical was applied with a micropipette on a ~1 cm diameter circle of skin, enclosed with a ring of cream [Baby cream "Nevskaya kosmetika Detskyi" Nevskaya Kosmetika Inc., Saint-Petersburg 192029], The number of shakes was counted for 1 hr after application.

The results for topical, perioral, and intravenous responses are summarized in Table 3. The surprising potency of DIPA-1-5 and DIPA-1-6 was unexpected but similar to what was seen with perioral administration. These smaller molecules may penetrate faster through the skin barrier and go into the systemic circulation. However, the value of this fast action is uncertain. In most contemplated topical applications of this discovery, the preference is for the drug action to remain localized and not systemic.

Intravenous. When the relative activities of the analogs for producing shaking by the perioral and topical routes were compared to the $EC_{50}$ for TRPM8 activation [as inversely measured by the xMenthol potency] it can be seen that the two variables are not correlated. For example, 2-6 is 4.7× menthol, but does not produce shaking by perioral or topical administration. Yet DIPA1-7, which 5.7× menthol, produces vigorous shaking by these routes. The lack of quantitative correlation is perplexing, because it would be expected that the cooling properties are linked to TRPM8 activation. To clarify the discrepancy, the test compounds were compared by the intravenous [i.v.] route of administration, a delivery route which is less influenced by membrane barriers.

Male rats weighing ~220-240 g were anesthetized with sodium pentobarbital, 55 mg/kg intraperitoneal, and after the loss of the righting reflex, animals were placed on a heated table and body temperature maintained at 37 to 38° C. The femoral vein was cannulated with PE-20 tubing connected to a 1 mL syringe. Stock solutions were prepared in normal saline at 10 mg/mL and further diluted to 2 mg/mL on the day of the experiment and injected at 0.1 mL/100 g body weight to give a dose of 1 mg/kg i.v. There were n=3 to 6 per test substance. Shaking frequency was counted for 30 min after i.v. delivery and the results compared with the Student's t-test. Two trials were conducted per animal with a 10 to 15 min interval between doses. The shaking frequency after intravenous injections is shown in Table 3.

Shaking was observed immediately after i.v. injection and at least 78% of the total shakes occurred in the first 5 min after injection. The response in the second trial was at least as robust in the first trial, showing the lack of desensitization [FIG. 3]. The greater response in the second trial may be due to cumulative effects or a lightening of anesthesia.

Figure 3:
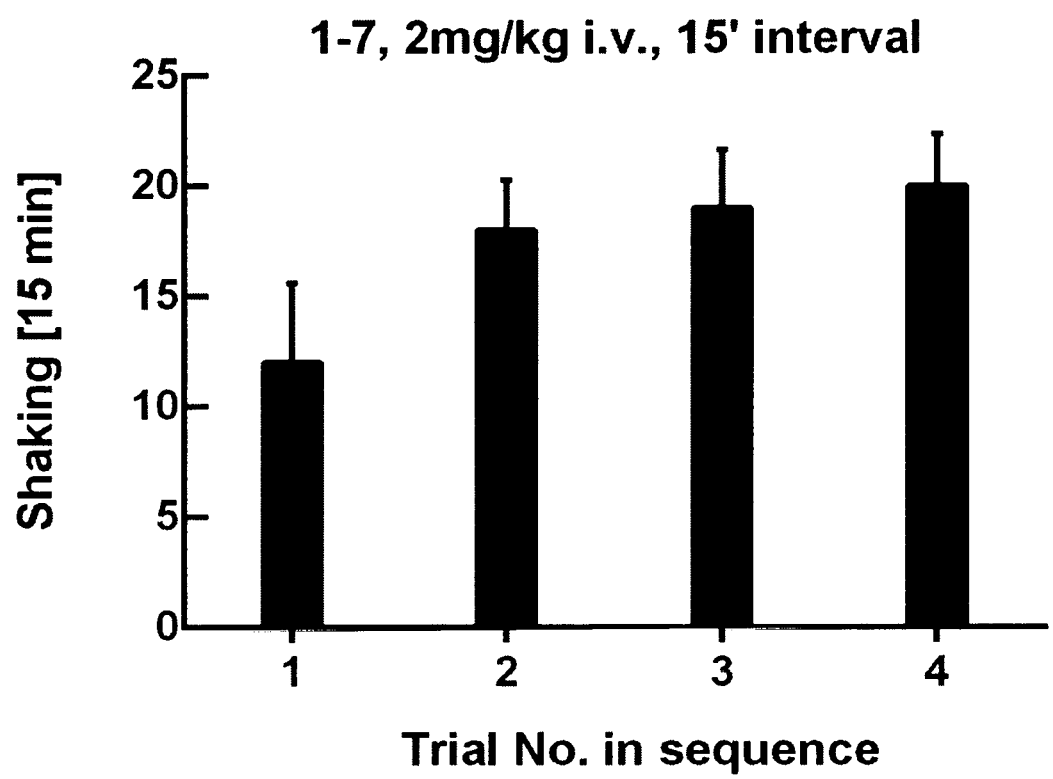
FIG. 3. is a graph showing the absence of tachyphylaxis to the shaking effects of repeated injections of DIPA-1-7, 2 mg/kg intravenous, at 15 min intervals. It can be seen that the shaking intensity of the $3^{rd}$ and $4^{th}$ trials were not diminished by the previous injections.

FIG. 3. shows the absence of tachyphylaxis [desensitization] to the shaking effects of repeated injections of DIPA-1-7, 2 mg/kg intravenous, at 15 min intervals. It can be seen that the shaking intensity of the $3^{rd}$ and $4^{th}$ trials were not diminished by the previous injections.

TABLE 3

Shaking frequency after perioral [per 20 mg/kg body weight] or topical delivery of 20 μl test compounds [per animal] or intravenously [2 mg/kg] to the anesthetized rat.

| Code | Mol Wt | # Cs | x Menthol | Perioral | Topical | Intravenous |
|---|---|---|---|---|---|---|
| DIPA-1-5 | 204 | 11 | 0.7 | 86 ± 7 | 138 ± 15 | 19 ± 3 |
| DIPA-1-6 | 218 | 12 | 1.6 | 56 ± 5 | 69 ± 8 | 39 ± 4 |
| DIPA-1-7 | 232 | 13 | 5.4 | 36 ± 4 | 79 ± 8 | 25 ± 3 |
| DIPA-1-8 | 246 | 14 | 5.4 | 0 | 7 ± 2 | 14 ± 2 |
| DIPA-1-9 | 260 | 15 | 4.0 | 0 | 0 | 3 ± 1 |
| 2-4 | 218 | 12 | 0.3 | 0 | 0 | 8 ± 2 |
| 2-5 | 232 | 13 | 2.2 | 4 ± 1 | 0 | 20 ± 2 |
| 2-6 | 246 | 14 | 4.7 | 0 | 0 | 30 ± 3 |
| 2-7 | 260 | 15 | 3.4 | 0 | 0 | 15 ± 2 |
| 2-8 | 274 | 16 | 2.9 | 0 | 0 | 2. |

Interpretation of $EC_{50}$ and Shaking Data After Perioral, Topical, and Intravenous Delivery The strong bioactivity of intravenous 2-6 and 2-7 is in sharp contrast to the results seen after perioral or topical delivery when no shaking was observed. These results provide strong objective laboratory evidence that the DIPA compounds of Table 1A are qualitatively different from the corresponding di-sec-butyl compounds. The diisopropyl compounds with the shorter $R_3$ chain produce shaking by all three routes of administration, whereas the di-sec-butyl compound is active only by intravenous delivery.

The TRPM8 $EC_{50}$ and perioral, topical, and intravenous provides an excellent framework and rationale for the selection of the best API for nasal discomfort.

The less potent candidates on the TRPM8 $EC_{50}$, namely, 1-5, 1-6, 2-4 and 1-10 were judged to be less suitable because of a lack of activation power.

The perioral and topical shaking seen with 1-5, 1-6 and DIPA-1-7 made these candidates less attractive because shaking is elicited by strong sensory stimuli, and this is not desirable in the nasal cavity. The extra penetrating quality of DIPA-1-7 may, however, be useful in congested situations such as the common cold and severe sinusitis.

The lack of activity of DIPA-1-8, DIPA-1-9, 2-6 and 2-7 on perioral and topical administration made these analogs attractive because it meant that these molecules remained localized in tissues after administration.

The greater shaking frequency see with 2-6 and 2-7 versus DIPA-1-8 and DIPA-1-9 meant that these molecules produced stronger sensations of cold, an effect which was confirmed on nostril skin.

From this analysis of the four measurements, namely, TRPM8 $EC_{50}$ and perioral, topical, and intravenous shaking activity, the logical initial choices for nasal discomfort is DIPA-1-8 and DIPA-1-9, followed by 2-6 and 2-7. DIPA-1-9 is especially attractive because it does not cause shaking, and yet is potent on the TRPM8 receptor.

Study 4

Screening of Compounds and Case Studies in Human Subjects

In these studies, subjects were given dosages units containing 1.5 to 1.75 mL of DAPA compounds stored in 2.0 mL microcentrifuge tubes (Nova Biostorage Plus, Canonsburg, Pa. 15317) and cotton swab (Puritan large cotton tipped applicators, Model 803-PCL) or SwabDose units, made by Unicep Corp., containing 2 mg/mL of DIPA-1-9. The tested compounds were as a solution in distilled water or in 1 mL of purified USP water. The range of tested concentrations was 1 to 4 mg/mL. The subjects were given instructions on how to place the tip of the applicator in the nostril, to gently compress the nostril with the thumb and forefinger to distribute the liquid into the anterior nasal vestibule. Approximately 0.03 mL to 0.06 mL is delivered by this method of application to the nasal cavity. A larger volume was occasionally delivered if the subject excessively wetted the cotton tipped applicator.

In a second set of experiments, the delivery system used was nose drops. Solutions were made up 0.1 to 5 mg/mL in isotonic saline and placed in 4 mL Nalgene 2752-9125 bottles which have a ½' tip than can be inserted past the nasal vibrissae, into the anterior nasal vestibule. With the head tilted slightly backwards, squeezing the bottle will reliably deliver ~40 μL per drop into the pocket formed at the base of the nares. Two to three drops were delivered per nostril. For example, for a 2 mg/mL DAPA compound the estimated delivered dose to both nostrils of the nose is 2 mg/mL×0.16 mL, or approximately 320 μg. This is comparable to the potency of intranasal steroids used for allergic rhinitis: for example, 55 μg of triamcinolone acetonide is delivered per actuation of a spray bottle of Nasacort® and the recommended dosing procedure is two actuations per nostril.

Three subjects, two with defined seasonal allergic rhinitis and one subject with chronic rhinitis of unknown cause, volunteered to be subjects for testing for multiple sessions. The compounds in Table 1 were tested when the subjects were symptomatic: i.e. were sneezing or had rhinorrhea, or had itchy sensations in the nose and eyes. The subjects refrained from the use of any antihistamine or intranasal steroids during the test periods, which lasted for six weeks. Subjects were instructed to rinse the nose with water if there was any nasal discomfort: however, irritation and discomfort was not seen in these trials.

These observations were made. The DIPA compounds 1-8 and 1-9 (1-[Diisopropyl-phosphinoyl]-octane and 1-[Diisopropyl-phosphinoyl]-nonane]), respectively, produced immediate, robust, and penetrating feeling of nasal clearing. The passage of air in the nostrils was refreshing and there was an absence of obstruction. For some subjects, sneezing and intranasal itching was inhibited within 5 to 10 min after application, and these effects were long-lasting: for 12 hr or more after a single instillation. But if the sneezing was on-going before instillation, the sense of clean breathing may also potentiate the sensation of itching in the nostrils. The consensus subjective feeling was, however, that nasal cavity discomfort was reduced and breathing felt clear and normal. The strong, efficacious drug action is unusual and has not been previously recognized to be achievable, and was surprising and amazing.

The two 1-[Di-sec-butyl-phosphinoyl]-alkanes of equal molecular weight and total number of carbons [14 and 15] to DIPA-1-8 and DIPA-1-9, namely, 2-6 and 2-7 1-[Di-sec-butyl-phosphinoyl]-hexane and 1-[Di-sec-butyl-phosphinoyl]-heptane], respectively, also exhibited efficacy. 2-6 and 2-7 had a stronger cooling action on the nasal mucosa and on the nostril skin after application. At higher doses, 2-6 and 2-7 sometimes triggered sneezing and long-lasting cooling on the skin on the tip of the nose. These side-effects may limit their use. But if nasal discomfort is not controlled by DIPA-1-8 or DIPA-1-9, then 2-6 and 2-7 are good back-up compounds.

For the other compounds, with total carbons numbers different from 14 or 15, good control of the symptoms of rhinitis was not achieved. For the two analogs with 13 carbons, DIPA-1-7 and 2-5, robust sensations were felt on the nostril skin and the nasal mucosa, but the beneficial effects on rhinitis were not evident. Both molecules seemed to induce rhinorrhea in some trials, perhaps reflecting a strong sensory action on cold receptors or on serous glands. For the two analogs with 16 carbons, 1-10 and 2-8, cooling sensations were minimally present after instillation, but there was little evidence of reducing the symptoms of rhinitis. In one subject 2-8 appeared to increase "stuffiness" at the higher concentration of 4 mg/mL.

These results of the various analogs, summarized in Table 4, are consistent with the TRPM8 $EC_{50}$ data, and the shaking data seen after intravenous, perioral and topical administration. The diminished activities of 1-10 and 2-8 are consistent with a lack of potency on TRPM8. DIPA-1-7 is very active on cold sensations and TRPM8, but its ability to penetrate and distribute in tissues is reflected in its shaking activity after perioral and topical administration. This is undesirable because the molecule will move away from its intended target site. DIPA-1-7 and 2-5 are both smaller molecules, having 13 carbons, and have greater mobility in tissues. Thus, DIPA-1-7 and 2-5 act on keratinized skin and do not localize well in the nasal cavity, and this limits efficacy.

The four compounds with 14 or 15 carbons, namely DIPA-1-8, DIPA-1-9, 2-6, and 2-7, are potent on TRPM8 and do not produce shaking after perioral or topical administration. This means that the drug is potent and also remains localized at its site of application: a highly desirable characteristic. Shaking may represent the ability of the molecule to produce a sensation of "stinging cold", and the diminished activity of DIPA-1-9 on this end-point makes it the lead candidate. DIPA-1-8 is the second lead candidate, followed by 2-6 and 2-7. The more intense cold seen with 2-6 suggests that it may be a preferred candidate for modifications of conditions such as sinusitis, heat stress, and "night sweats". In these conditions, a stronger sense of cold may have better therapeutic value.

In summary, the pattern of activity of each molecule is a sum of penetration, distribution, localization, and intrinsic activity at the receptor. The best compounds are those that have potency on the nasal mucosa, and not on the keratinized skin of the nares and nasal vestibule The best compounds of the present discovery for nasal discomfort are DIPA-1-8 and DIPA-1-9, and 2-6 and 2-7, and are examples of 1-[Dialkyl-phosphinoyl]-alkanes [(O=)$PR_1R_2R_3$] wherein each of $R_1$, $R_2$, is either isopropyl or sec-butyl and $R_3$ is a linear alkyl group of 6 to 9 carbons, and wherein the preferred embodiments have 15 or 16 carbons.

Case studies are described below which illustrate the use of several DAPA compounds delivered to the nasal cavity. The preferred embodiments are effective:
  to reduce the discomfort of allergic rhinitis;
  to reduce the discomfort of vasomotor rhinitis;
  to reduce sneezing and rhinorrhea;
  to enhance the sense of breathing fresh air in normal subjects;
  to reduce the discomfort of breathing polluted air;
  to enhance breathing comfort and performance in a professional athlete;
  to help an individual cope with heat stress; and
  to reduce the severity of "night sweats" in a subject.

TABLE 4

Test Results of Compounds on Nasal Discomfort Caused by Rhinitis

| Chemical Code | No. Carbons | Mol.Wt. | Efficacy | Side-effects |
| --- | --- | --- | --- | --- |
| DIPA-1-7, 2-5 | 13 | 232.34 | + | cold, rhinorrhea |
| DIPA-1-8, 2-6 | 14 | 246.37 | +++ | cold skin for 2-6 |

TABLE 4-continued

Test Results of Compounds on Nasal Discomfort Caused by Rhinitis

| Chemical Code | No. Carbons | Mol.Wt. | Efficacy | Side-effects |
|---|---|---|---|---|
| DIPA-1-9, 2-7 | 15 | 260.40 | +++ | cold skin for 2-7 |
| DIPA-1-10, 2-8 | 16 | 274.44 | 0 | congestion |

Study 5
Combination of DAPA Compounds and Medications in Various Intranasal Sprays.

The primary goals of these experiments were to:
Determine if the selected cooling agent was chemically compatible with the nasal medication containing an intranasal steroid or intranasal antihistamine: that is, if the two items could be homogeneously mixed in solution without the appearance of precipitates. Other intranasal medications, such as isotonic and hypertonic saline, cromolyn sodium and phenylephrine HCl, were also examined.

Find a concentration and regimen of the selected cooling agent in the combination that will impart a rapid strong refreshing sensation capable of relieving the sense of nasal congestion. This study was first conducted in individuals without rhinitis and then in individuals with symptoms of allergic rhinitis.

Ascertain if the selected cooling agent in rhinitis patients will improve adherence in the use of the intranasal steroid or intranasal antihistamine and improve treatment outcome.

Standard approved over-the-counter intranasal steroids in the USA are Nasacort®, Flonase®, and Rhinocort® containing the active ingredients of triamcinolone acetonide, fluticasone propionate (or furoate), and budenoside, respectively. These OTC bottles or their international equivalent were obtained and a cooling agent was added to the preparation and the bottle coded. The bottles were then shaken and examined to ensure thorough mixing of the contents. The test solutions, for example, of triamcinolone acetonide preparation had a cloudy/milky appearance, thus mixing was examined under intense light to ascertain homogeneous distribution of the cooling agent when added into solution. The concentrations of the cooling agent chosen for combination ranged from 1 to 10 mg/mL for the final concentrations selected as shown in the Tables. The amphiphilic characteristic of the preferred embodiments gave the mixed solution a bubbly appearance which was not seen with the vehicle control (water). These bubbles further confirmed the presence of cooling ingredient in the combination.

Subjects without rhinitis given the coded preparations (with or without cooling agent) were asked to rate the medication on tastes, quality and intensity of cool sensations, and the feeling of nasal patency. These tests were then repeated in patients with allergic rhinitis. For the individuals with rhinitis, a standardized total nasal symptom score (TNSS) questionnaire was administered every two days, and the bottles weighed at that time. These procedures were repeated over a total 5-day period of study. The weights of the bottle (weights of medications consumed or WMC) measure the number of actuations that were used by the subject and indicate adherence/compliance. The five DAPA compounds selected for study were DIPA-1-7, DIPA-1-8, DIPA-1-9, DAPA-2-6, and DAPA-2-7. A standard questionnaire was used to record the TNSS at two day intervals.

Combination of DAPA Compounds and Intranasal Steroids

The tested intranasal steroids were commercial formulations of triamcinolone acetonide and of beclometasone dipropionate. The dosage recommendations for these formulations are 2 actuations of the nasal pump once daily for triamcinolone acetonide, and 1 actuation of beclometasone dipropionate 2 times per day. The results are shown in Table 5 and 6. One can conclude that a DAPA cooling agent, added to a standard formulation of an intranasal steroid spray, imparts an immediate sense of refreshing coolness in the nasal cavity.

TABLE 5

Test of Intranasal Steroid Spray with Cooling Agent Adjunct*

| Agent | Steroid | Effects |
|---|---|---|
| Vehicle** | Triamcinolone Ac*** | No sensations of coolness or refreshment were reported after use of the spray. |
| DIPA-1-9 5 mg/mL** | Triamcinolone Ac*** | Refreshing cool/cold were immediately obtained in the nasal cavity, lasting ~0.5 to 0.75 hr. No discomfort was reported and no rhinorrhea was observed in the four tested subjects. |
| DIPA-1-9 10 mg/mL** | Triamcinolone Ac*** | Robust stinging cool/cold sensations were obtained in the nasal cavity, lasting ~1 hr. There was rhinorrhea in two of the four tested subjects. |

*Tests were conducted in 4 normal volunteers without rhinitis. Subjects sprayed the preparation once a day for 3 consecutive days and filled in a questionnaire form each day with comments on the observed drug actions.
**The vehicle was distilled water (0.1 mL). The test materials were added 50 mg or 100 mg directly to the liquid in the nasal spray bottle.
***Triamcinolone Nasal Spray –24 hr, made by XingYin Company in NanJing China, registration number 20020360. Each bottle contained 11 mg of triamcinolone acetonide in a 10 mL liquid composition. The total dose per two actuations per both nostrils was 220 µg or equivalent to a total dose of 0.2 mL of the solution, or 0.1 mL per nostril. Actual measurements of volume per two actuations showed a range of 0.095 to 0.011 mL with an average of 0.099 mL ± 0.001 (SD, n = 200 actuations).

TABLE 6

Test of Intranasal Steroid Spray with Cooling Agent Adjunct*

| Agent | Steroid | Effects |
|---|---|---|
| Vehicle** | Beclometasone dipropionate*** | No sensations of coolness or refreshment were reported after use of the spray. |
| DIPA-1-8 5 mg/mL** | Beclometasone dipropionate*** | Refreshing cool/cold sensations were immediately obtained in the nasal cavity, lasting ~0.5 to 0.75 hr. No discomfort was reported and no rhinorrhea was observed the four tested subjects. |
| DIPA-1-9 5 mg/mL** | Beclometasone dipropionate*** | Refreshing cool/cold sensations were immediately obtained in the nasal cavity, lasting ~0.5 to 0.75 hr. No discomfort was reported and no rhinorrhea was observed the four tested subjects. |

*Tests were conducted in 4 normal volunteers without rhinitis. Subjects sprayed with one actuation twice a day for 3 consecutive days and filled in a questionnaire form each day with comments on the observed drug actions.
**The vehicle was distilled water (0.1 mL). The test materials were added 50 mg directly to the milky/cloudy liquid in the nasal spray bottle. Rinoclenil ® contains phenylethylalcohol as an excipient.
***Beclometasone dipropionate Rinoclenil ® Nasal Spray, made by Chiesi, Parma, Italy, registration number 3400937071024. One actuation per nostril, twice daily is expected to deliver 100 µg of beclomethasone dipropionate. A similar product, called Humex, was also tested with similar results.

Combinations of DAPA Compounds and Intranasal Antihistamine

Azelastine HCl is an effective intranasal antihistamine. The complete miscibility of the DAPA compounds in the colorless liquid of a commercial preparation of azelastine chlorohydrate (Allergodil®) was noted, and showed compatibility of the combination of the two ingredients. The strong bitter tastes of azelastine sprays have been found in previous studies of this topical antihistamine (Seidman et al. vide supra) but are not observed with the intranasal steroid sprays. Surprisingly, the cooling agents tested here, especially DIPA-1-9, reduced the intensity of the azelastine bitterness (Table 7). This effect was also found when the spray was applied directly into the oral cavity. The acute bitterness was attenuated, although there was some lingering bitterness afterwards. The azelastine spray was well-accepted in rhinitis patients and reduced the TNSS scores, especially in the category of nasal itching. From these results, one can conclude that a DAPA cooling agent can be added to a standard formulation of an intranasal antihistamine spray to impart an immediate sense of refreshing coolness in the nasal cavity.

TABLE 7

Test of Intranasal Antihistamine Spray with Cooling Agent Adjunct*

| Agent | Antihistamine | Effects |
|---|---|---|
| Vehicle** | Azelastine HCl*** | No sensations of coolness or refreshment were reported after use of the spray. In three out of four subjects, a strong bitter taste was noticed on the tongue. |
| DAPA-2-6 5 mg/mL** | Azelastine HCl*** | Refreshing cool/cold sensations were immediately obtained in the nasal cavity, lasting ~0.5 to 0.75 hr. No discomfort was reported and no rhinorrhea was observed the four tested subjects. |
| DIPA-1-9 8 mg/mL** | Azelastine HCl*** | Refreshing cool/cold sensations were immediately obtained in the nasal cavity, lasting ~1 hr. No discomfort was reported and no rhinorrhea was observed the four tested subjects. Surprisingly, no subjects reported bitter taste. |

*Tests were conducted in 4 normal volunteers without rhinitis. Subjects sprayed with one actuation twice a day for 3 consecutive days and filled in a questionnaire form each day with comments on the observed drug actions.
**The vehicle was distilled water. The test materials were added ~120 mg directly to the clear liquid in the nasal spray bottle (~13 mL) Allergodil ® is a clear colorless liquid and completely miscible with DIPA-1-9 at the tested concentration of 9 mg/mL of DIPA-1-9.
***Azelastine chlorohydrate Allergodil ® Nasal Spray, made by Meda Pharma, Paris, France. registration number 56FR22025007-00. One actuation per nostril is expected to deliver 0.125 mg/dose of active substance. The single actuation delivered ~0.135 mL of liquid.

Combination of DAPA Compounds With Intranasal Saline

Distilled water administered into the nasal cavity produces an acute sense of discomfort, most likely because of an osmotic effect on the sensitive cells of the nasal membranes. The unpleasant effect is immediate and noxious, but does not last more than a few minutes. It is similar to getting water into the nose in a swimming pool. Isotonic saline or hypertonic saline, containing 0.9 g or 2.65 g of sodium chloride per 100 mL of water, respectively, do not produce this osmotic effect and are used as nasal sprays and rinses. The saline solutions sprayed into the nasal cavity do not irritate the nasal membranes or produce cooling sensations. The efficacy of these saline solutions on the treatment rhinitis is not robust, but have a flushing and cleansing action of the nasal cavity.

Here a range of DAPA compounds 0.5 to 5 mg/mL were added to irrigation solutions of isotonic or hypertonic saline and administered as a spray in single or double actuations of 0.1 mL per actuation, or administered as a nose drop using eye dropper bottles with an extended tip that reliably releasing 0.04 mL per drop per squeezing. For the nose drops, the number squeezed into the nostril was 2 to 3 drops, or about 0.1 mL per nostril. The results are shown in Table 8.

The DAPA compounds administered via spray or drops in saline solutions all produced immediate refreshing and clearing sensations in the nasal cavity. All subjects opined that breathing was immediately cleared, within 0.5 to 2 min of dosing. This was seen in normal subjects and in subjects with allergic rhinitis. The duration and intensity of coolness varied with dose and compound. DIPA1-7 had the fastest onset and cooling intensity, but at 5 mg/mL, it was also produced a mild degree of rhinorrhea. DIPA-1-9 had the longest duration of action, for several hours, and in some subjects using nose drops the sense of clearance lasted the whole day after administration. Case studies are further detailed below. It is apparent, that addition of a DAPA compound to a saline composition, containing 0.9 to 2.65 g of sodium chloride per 100 mL water mixes well and provides immediate relief for a congested nose. A robust cooling effect can be obtained by spray or by nose drops. The DAPA compounds, at the tested concentrations of 0.5 to 5 mg/mL, are completely miscible and compatible with the saline solutions.

TABLE 8

Testing of Intranasal Irrigation Solutions with Cooling Agent Adjunct*

| Agent | Irrigation solution | Effects |
|---|---|---|
| Vehicle** | Distilled water*** | Distilled water alone produced an immediate sense of irritation and discomfort in four out of four subjects. Testing of this solution was discontinued. |
| DAPA-1-8 5 mg/mL + NaCl, 0.9% | Isotonic saline*** | Robust cooling was felt but no discomfort was reported and no rhinorrhea was observed in the four tested subjects. |
| DAPA-1-9 5 mg/mL + NaCl, 2.65% | Hypertonic saline*** | Robust cooling was felt but no discomfort was reported and no rhinorrhea was observed in the four tested subjects. |

*Tests were conducted in 4 normal volunteers without rhinitis. Subjects sprayed with two actuations twice a day for 3 consecutive days (for the isotonic and hypertonic saline experiments) and filled in a questionnaire form each day with comments on the observed drug actions.
**The vehicle was distilled water. Sodium chloride was added to the distilled water to make up the isotonic or hypertonic saline. Ayr ® allergy and sinus hypertonic saline nasal mist is an example of a product line in the "saline" category and contains 2.65% sodium chloride. The DAPA compounds are completely soluble in saline at the tested concentrations of 1 to 5 mg/mL. Saline nose drops containing DAPA compounds could also be used with immediate onset of cooling.
***One actuation per nostril delivered volume of ~0.106 mL of saline solution.

Combination of DAPA Compounds With Other Intranasal Medications

Cromolyn sodium is a "mast cell stabilizer", i.e. it inhibits the release of inflammatory mediators from the mast cell, principally histamine. Histamine in the nasal cavity causes itch and sneezing and increases blood flow and vascular permeability that lead to rhinorrhea. Cromolyn sodium is available as an OTC drug, with 2.5 mg delivered per actuation. The recommended procedure, e.g. for Nasal-Crom®, is to spray 3 to 4 times day, with a maximum of 6 times. On the package insert, it is noted that users of NasalCrom® may take several days to notice a beneficial effect and full effect is not seen until 1 to 2 weeks. Cromolyn sodium is considered active and safe, but it is not the drug of first choice for allergic rhinitis because of its perceived limited efficacy (Seidman et al. vide supra). Experimentally, it is shown here that two DAPA compounds, added to NasalCrom® is chemically miscible, and that an immediate cooling effect is obtained after spraying. NasalCrom® alone does not produce cooling. The results are shown in Table 9.

TABLE 9

Testing of Intranasal Mast Cell Stabilizer with Cooling Agent Adjunct*

| Agent | Mast Cell Stabilizer | Effects |
|---|---|---|
| Vehicle** | NasalCrom®*** | No irritation or discomfort was reported after use of the spray in four out of four subjects. There were also no sensations of coolness. |
| DAPA-2-7 5 mg/mL | NasalCrom®*** | No discomfort was reported and no rhinorrhea was observed in the four tested subjects. Immediate sensations of cooling or cold were noted. |
| DAPA-2-6 5 mg/mL | NasalCrom®*** | No discomfort was reported and no rhinorrhea was observed in the four tested subjects. Immediate sensations of cooling or cold were noted. |

*Tests were conducted in 4 normal volunteers without rhinitis. Subjects sprayed with one actuation three times a day for 3 consecutive days.
**The vehicle was distilled water. DAPA-2-5, DAPA-2-6 was added to NasalCrom®, a preparation containing cromolyn sodium, benzoalkonium chloride, edetate disodium, and purified water. The NasalCrom® solution was a clear and transparent liquid. The DAPA compounds were completely soluble in the NasalCrom® at the tested concentrations of 2 to 5 mg/mL.
***One actuation per nostril delivered volume of ~0.134 mL.

The α-adrenergic sympathomimetic decongestants (e.g. phenylephrine, oxymetazoline, napthoazoline) act on vascular smooth muscle to cause constriction and thereby limit blood flow to the vessels of the nasal cavity. The reduced blood volume of the nasal cavity lowers resistance to airflow and relieves nasal congestion. These nasal sprays come with the warning of "do not use for more than three days" because of the risks of rebound hyperemia (rhinitis medicamentosa), when usage is stopped. In spite of this rebound danger, these "decongestant" solutions are widely available. Here, we show that two DAPA compounds are compatible with a commercial preparation of 1% phenylephrine HCl. Immediate cooling was observed when a DAPA compound was added to the phenylephrine HCl preparation. The results are shown in Table 10.

TABLE 10

Testing of Intranasal Decongestant with Cooling Agent Adjunct*

| Agent | Decongestant | Effects |
|---|---|---|
| Vehicle** | Phenylephrine HCl*** | No irritation or discomfort was reported after use of the spray in four out of four subjects. There were also no sensations of coolness. |
| DIPA-1-9 5 mg/mL | Phenylephrine HCl*** | No discomfort was reported and no rhinorrhea was observed in the four tested subjects. Immediate sensations of cooling or cold were noted. |
| DAPA-2-6 5 mg/mL | Phenylephrine HCl*** | No discomfort was reported and no rhinorrhea was observed in the four tested subjects. Immediate sensations of cooling or cold were noted. |

*Tests were conducted in 4 normal volunteers without rhinitis. Subjects sprayed with one actuation three times a day for 3 consecutive days.
**The vehicle was distilled water. DAPA-2-5, DAPA-2-6 was added to Extra Strength Sinus Relief, CVS Health, containing phenylephrine hydrochloride 1.0%. The DAPA compounds are completely soluble in this solution at the tested concentrations of 5 mg/mL.
***One actuation per nostril delivered volume of ~0.078 mL.

Study 6
Efficacy of Combinations in Adherence/Compliance and in Treatment of Rhinitis From the previous experiments, it was concluded that DAPA compounds can be combined with standard intranasal medications to obtain a cooling effect with rapid, immediate onset and a sense of open breathing. Further studies were conducted on allergic rhinitis patients using combinations with nasal sprays containing triamcinolone acetonide (Xin-Yang Company) and azelastine HCl (Meda Pharmaceuticals). The goals were to determine adherence/compliance and efficacy of these combinations.

The measurement of adherence/compliance was the "weight of medications consumed (WMC)", that is, the weight of the spray bottle before and after a 5 day period of use [Loh et al. A clinical survey on compliance in the treatment of rhinitis using nasal steroids, *Eur. J. Allergy Clin. Immunol.* 59, 1168-1172 (2004)]. It was found that the WMC was greater by 33% in the triamcinolone group and by 40% in the azelastine group if the cooling agent was present. The main reason given by the subjects for more frequent use of the DAPA combination was because the subjects liked the immediate drug effect and hence were less likely to forget to spray. The TNSS was also improved in the group that received the cooling agent combination: by 28% in the triamcinolone group and by 45% in the azelastine group. The triamcinolone group objected to the "soapy" feel of the steroid spray and thereby used it less often. By contrast, the azelastine group felt immediate relief and was enthusiastic in adherence without, surprisingly, any complaints of bitter tastes.

In four of the six subjects in the cooling agent/azelastine group, there was also the opinion that the "allergic rhinitis" condition had permanently been reduced in severity. These individuals continued to use the combination beyond the 5-day trial period on an as needed basis. The results suggested the combination may have a disease-modifying effect on allergic rhinitis in addition to immediate symptomatic relief of itch, sneezing, rhinorrhea, and a feeling of nasal congestion. Some of these cases are described further in the examples.

Case Study 1.

A 70-year old male subject had long-standing seasonal allergic rhinitis since he first noticed nasal symptoms on a golf course in spring, 45 years ago. The likely trigger was grass pollen because the allergy manifested itself most often after rainstorms followed by periods of dry weather. Over the years, he learned to control nasal congestion and rhinorrhea with oral antihistamines by taking a daily dose of 10 mg of loratadine, supplemented during the hay fever season by two 60 mg fexofenadine tablets daily, and when necessary 5 mg of chlorpheniramine. He had tried an intranasal steroid spray [Flonase®], but found the delivery method "messy" and leaving objectionable sensations in the nose and mouth which interfered with gustation.

This season his allergy was heralded by the onset of severe bouts of violent sneezing, about 10 to 15 sneezes in a 15 min period, followed by rhinorrhea and congestion. He volunteered to try the DAPA compounds of this discovery and stopped using oral antihistamines. He started with a DIPA-1-9 2 mg/mL swab and right away noticed the disappearance of sneezing and rhinorrhea which lasted for at least 12 hr. He found that a single daily DIPA-1-9 1 mL swab was sufficient to block all symptoms of hay fever. No odor, irritation, or taste was detected from the swab. The individual had a sense of free and unobstructed airflow in the nasal cavity. He no longer used any oral antihistamines.

This individual then volunteered to repeat the experience with other analogs with some of the results as shown in Table 5. He noted the cooling effects of 2-6 and 2-7 on the nostril skin, and some initial itching and rhinorrhea with these compounds. But he was also sure that these analogs were effective in preventing the symptoms of hay fever. He tried swabs with DIPA-1-8 at a higher concentration of 4 mg/mL and waited for hay fever symptoms to recur. To his surprise, symptoms did not recur until after 5 days. He said it was as if the drug had cured the disease. His wife also noted that he had stopped snoring and snorting during sleep when he was using the swabs. Swabbing with just distilled water was not effective in controlling his hay fever symptoms. He pronounced his cure as being "miraculous" because the rhinorrhea disappeared, although he still had an occasional sneeze. The only side effect he noted from the DAPA compounds was occasional stuffiness because of crusted and dried mucus on his nasal membranes. This problem was easily solved by rinsing his nose with tap water.

Case Study 2.

A 50-year old male subject is a distinguished scientist at a world-renowned institute of research in physiology. He has a MD and a PhD degree. The subject suffers from perennial rhinitis of many years. He stated that the rhinorrhea is "always there" and seeing specialists and taking standard medications such as intranasal steroids and antihistamines were minimally effective to help control the symptoms. He noted that on average his rhinorrhea can be estimated by the 10 Kleenex tissues he deposits each day into his waste paper basket! He volunteered to try swabs containing DIPA-1-9, 2 mg/mL and was given instructions on how to apply the solution onto the anterior nasal vestibule. He reports that "The results are truly amazing. For the first time in many years, I woke up in the morning without any rhinorrhea." He noted that he now uses zero or only one or two Kleenex tissues for his nose each day. He remarked on the "strong drying effect on the mucous membranes of the nasal cavity after repeated use" and suggested that there might be an inhibitory drug effect on serous gland secretion in the nasal mucosa. When asked if he felt coolness or cold when applying DIPA-1-9 2 mg/mL into his nostril, he said "neither term is correct; the sensation is of comfortable freshness." He was of the opinion that a slightly higher concentration, e.g. 3 or 4 mg/mL of DIPA-1-8 or DIPA-1-9 instead of 2 mg/mL might be more effective in gaining full control of his rhinorrhea.

A 65-year old male is retired and lives in Las Vegas, in a gated community with a golf course. But during spring he suffers severely from allergic rhinitis and allergic conjunctivitis. The conjunctivitis is especially annoying because he likes to play in professional poker tournaments. He volunteered to try the DIPA-1-9 2 mg/mL swabs and noted that it worked well for his rhinitis. Surprisingly, he also found that his pruritic conjunctivitis was relieved. Upon closer questioning, it was clear that he did not apply the swabs to his eyes but had used generous amounts in his nasal cavity. He had been instructed to squeeze his nostrils gently to disperse the liquid after applying the swab to the anterior nasal vestibule. Apparently, he had applied too much liquid and squeezed the applied droplets so that there was retrograde flow up the nasal-lachrymal duct so that his eyelids received the DIPA-1-9 formulation. He remarked that his eyelids felt cool and comfortable and the itchiness in his eyes was gone.

A 55-year old male subject manifested severe and persistent nasal congestion. He was diagnosed as having chronic rhinosinusitis and endoscopic sinus surgery was recommended, but he was reluctant to undergo this procedure. He blamed his condition on not taking good care of his allergic rhinitis during his youth. All attempts at previous medical therapy were not successful. He tried the isotonic saline nose drops containing 2 mg/mL of DAPA-1-9 and pronounced the clearing effect as a "miracle". He said that now he could sleep well at night. He used the nose drops on an as needed basis for two weeks, but decided that he was not "cured" and agreed to try a combination of DAPA-1-9/azelastine hydrochloride combination. After two weeks of use, he said that his nasal congestion had diminished to the point where he only needed to use the nose drops on an occasional basis. He said the drug effect qualified as a "disease-modifying effect."

Case Study 3

A 45-year old female subject was a professional tennis player. She had nasal congestion from the common cold before an important match and asked if she could try the swab. She was given a swab containing 4 mg/mL of 2-6. She said the swab was fully effective in reducing her congestion and she was very pleased that she won her match. Subsequently, she went to Hong Kong to visit her grandfather. It was in February and she noted the air pollution was severe, and going out into the streets gave her the sniffles. She had been given swabs containing DIPA-1-9 2 mg/mL and she said use of these swabs reduced the irritant effects of breathing the polluted air.

The efficacy of the swabs in controlling the symptoms of nasal stuffiness from the common cold was confirmed in two other subjects. The effects, however, were not as dramatic as with hay fever symptoms. One subject remarked that when "The nose was completely stuffed up, it was difficult to inhale and self-administer the contents of the swab." It is more likely that the common cold virus causes a wider area of inflammation on the turbinate mucosa, and hence the medication needs to have a wider distribution to abrogate the sense of stuffiness. Nevertheless, there was a beneficial effect on the subjective symptoms of congestion from the common cold.

Case Study 4

A 45-year old male subject with severe seasonal rhinitis volunteered to test various substances by intranasal swab delivery. He had previously tried the Zicam Nasal Swabs for "gentle Allergy Relief" but noted that the gel on the swabs felt a little bit "slippery" and uncomfortable when applied to the nasal cavity. He said that the instructions and information on the Zicam box was "use 1 tube every 4 hours" and "optimal results may not be seen for 1 to 2 weeks." He said that the gel congealed after opening in less than 24 hr so it was not possible to use the same swab for multiple applications.

He tried the DIPA-1-9 2 mg/mL swab with and without the addition of CPS-030 5 mg/mL. He noted that the CPS-030 added swab had a faster onset of cooling action, but may have also increased his rhinorrhea. Monomenthyl glutarate and Cooler 10 added to DIPA-1-9 at 8 mg/mL did not enhance efficacy when tested in this subject. The DIPA-1-9 swab, however, effectively controlled his symptoms, especially the sneezing, with an immediate onset of effect. He only had to use the same swab and apply it twice a day to gain complete control of his symptoms. This subject remarked that icilin powder, inhaled from the radial fossa, was still the best medication for him because one dose was sufficient for 24 hr control of his symptoms. He recommended that the icilin powder be added to the DIPA-1-9 swab. Overall, he was very pleased with the efficacy of the DIPA-1-9 swab.

Case Study 5

A 49-year female subject went for a month vacation to the South of France in March when the mimosa and cypress trees were in full bloom and developed severe symptoms of allergic rhinitis. She had vigorous bouts of sneezing and profuse nasal secretions, and used up box after box of Kleenex tissues. Oral antihistamines such loratadine, cetirizine, chlorpheniramine, and fexofenadine were not effective, in part because she did not adhere to a carefully regulated dosing regimen. She tried a intranasal steroid spray but complained that it gave her a messy "greasy" feeling in her nasal secretions. After using nose drops containing DAPA-1-9 in isotonic saline and a nasal spray of DAPA-1-9 combined with azelastine HCl, her symptoms were controlled within 24 hr and she was able to resume her normal activities. She remarked that the cooling sensation and immediate relief of nasal congestion from the combination product enabled her to follow a structured self-dosing schedule.

In summary, a class of DAPA compounds with cooling effects have been identified that can be combined with standard intranasal medications that are used to treat the nasal discomforts associated with rhinitis. These molecules are water soluble and compatible current topical intranasal medications such as intranasal steroids and intranasal antihistamine. The combinations are used to enhance the efficacy of the medications and to improve patient adherence to a dosage regimen.

REFERENCES

A number of publications are cited herein in order to more fully describe and disclose the discovery and the state of the art to which the discovery pertains. Each of these publications is incorporated herein by reference in its entirety into the present disclosure.

The invention claimed is:

1. A method for relieving sensory discomfort caused by allergic or perennial allergic rhinitis in a subject, comprising:
    intranasally administering to the subject in need thereof a therapeutically effective amount of a composition in a liquid solution comprising 1-[Diisopropyl-phosphinoyl]-nonane and azelastine hydrochloride, the amount of 1-[Diisopropyl-phosphinoyl]-nonane being at a concentration of 1 to 10 mg/ml, the amount of composition administered being therapeutically effective to reduce nasal congestion.

2. The method as in claim 1 wherein the composition is in the form of an aerosol, nasal drops, a nasal spray or an irrigation solution.

3. The method as in claim 1 wherein azelastine hydrochloride administered is in an amount of about 0.1 to 5 mg/mL.

4. The method as in claim 1 wherein the liquid solution is an isotonic or hypertonic saline solution.

5. The method as in claim 1 wherein the administering leads to an increased compliance or adherence to use of the composition by the subject.

6. A method of increasing compliance or adherence to treatment in a patient in need of an intranasal medication for the treatment of sensory discomfort in a nasal cavity caused by allergic or perennial allergic rhinitis, comprising:
    providing an aqueous liquid composition having a therapeutic amount of 1-[Diisopropyl-phosphinoyl]-nonane therein and azelastine hydrochloride, wherein the therapeutic amount of 1-[Diisopropyl-phosphinoyl]-nonane is a concentration of 1 to 10 mg/mL in the liquid composition, the aqueous liquid composition being a hypertonic saline solution, or an isotonic saline solution;
    instructing a user in intranasally administering said composition; and
    administering the composition to said patient.

7. The method as in claim 6 wherein the instructing provides for the administering of from about 0.1 to 5 mg/mL of azelastine hydrochloride.

8. The method as in claim 6 wherein the therapeutic amount of 1-[Diisopropyl-phosphinoyl]-nonane is therapeutically effective to reduce nasal congestion in less than about two minutes.

* * * * *